(12) United States Patent
Saraya

(10) Patent No.: US 6,523,193 B2
(45) Date of Patent: Feb. 25, 2003

(54) PREVENTION SYSTEM AND PREVENTING METHOD AGAINST INFECTIOUS DISEASES, AND APPARATUS FOR SUPPLYING FLUIDS

(75) Inventor: Ichiro Saraya, Osaka-fu (JP)

(73) Assignee: Saraya Co., Ltd., Osaka-fu (JP)

( * ) Notice: Subject to any disclaimer, the term of this patent is extended or adjusted under 35 U.S.C. 154(b) by 0 days.

(21) Appl. No.: 09/977,354

(22) Filed: Oct. 16, 2001

(65) Prior Publication Data

US 2002/0050006 A1 May 2, 2002

(30) Foreign Application Priority Data

Oct. 17, 2000 (JP) ........................................ 2000-317224
Jan. 10, 2001 (JP) ........................................ 2001-002591

(51) Int. Cl.$^7$ ................................................ E03C 1/05
(52) U.S. Cl. ........................ 4/623; 4/262; 4/628; 4/668
(58) Field of Search ......................... 4/262, 263, 518, 4/569, 591, 619, 623, 624, 625, 626, 628, 638, 668, 678; 433/88, 97

(56) References Cited

U.S. PATENT DOCUMENTS 1,424,272 A  *  8/1922  Ankeny ......................... 4/262
2,310,617 A  *  2/1943  Conner .......................... 4/624
4,606,085 A  *  8/1986  Davies .......................... 4/623
4,942,631 A  *  7/1990  Rosa ............................. 4/623
5,031,258 A  *  7/1991  Shaw ............................. 4/623
5,199,118 A  *  4/1993  Cole et al. .................... 4/619
5,670,945 A  *  9/1997  Applonie .................... 4/619 X
5,690,255 A  * 11/1997  White ......................... 222/135

* cited by examiner

Primary Examiner—Robert M. Fetsuga
(74) Attorney, Agent, or Firm—Wenderoth, Lind & Ponack, L.L.P.

(57) ABSTRACT

The present invention provides a system and method of effectively preventing infection, and provides a fluid supply apparatus capable of being preferably used for the system. A fluid supply apparatus is disposed near a doorway of a hall of an ordinary household. The fluid supply apparatus includes a water supply function performed by a water supply nozzle, a gargle discharge function performed by a gargle nozzle, a disinfectant discharge function performed by a disinfectant nozzle, and a sink. A body detection sensor for detecting a human body that enters a room is provided above the doorway. When the body detection sensor detects a body, a voice output apparatus outputs a voice prompting the person to gargle and wash hands.

16 Claims, 15 Drawing Sheets

Y16        Y16

PREVENTION SYSTEM AND PREVENTING METHOD AGAINST INFECTIOUS DISEASES, AND APPARATUS FOR SUPPLYING FLUIDS

BACKGROUND OF THE INVENTION

The present invention relates to a prevention system and a method of preventing infectious diseases, that is applied suitably in an ordinary home or a facility such as a hospital, a food factory and the like. Furthermore, the present invention relates to an apparatus for supplying fluids that can be suitably used for a prevention system and a method of preventing infectious diseases.

As is well known, gargling, washing hands, and disinfecting fingers with a disinfectant are encouraged in medical facilities such as hospitals, in order to prevent infectious diseases such as MRSA (methicillin resistant Staphylococcus aureus), VRE(vancomycin resistant Entrococcus) and the like. It is possible to an extent to prevent people from being infected by infectious diseases in medical facilities such as hospitals by striving for gargling and washing hands. However, now in an aging society, there also is a fear of becoming infected with infectious diseases in an ordinary home or household since what is called home nursing is increasing.

Influenza often prevails when the seasons change. It is known that gargling and washing hands are effective for preventing an infectious disease such as influenza. Furthermore, it is known that gargling and washing hands when getting home from outside improve the patient's ability to prevent an allergic disease such as hay fever (a pollinosis).

As mentioned above, gargling and washing hands is effective for preventing infectious diseases and allergic diseases. In particular, people can effectively prevent being infected by an infectious disease by gargling and washing hands before taking off their shoes just after they get home.

The gargling and washing hands are usually conducted by using a sink and a water supply function provided in a washroom. However, in an ordinary household, since the washroom is usually located far from an entrance, it is troublesome for an inhabitant to go directly to the washroom just after coming home from outside, or he is apt to forget to do so. Therefore, it is hard to expect that gargling and washing hands will be reliably conducted before taking off one's shoes just after one gets home.

Furthermore, in a facility such as a food factory and the like, usually the employees have to gargle and wash their hands as a matter of course before they start to work in the factory. However, in a case where a washroom for gargling and washing hands is not located near an entrance to the factory, there is a fear that they will forget to gargle and wash their hands.

As an apparatus which is to be placed in a washroom for gargling and washing hands, there is a known apparatus provided with a plurality of fluid supply mechanisms for supplying different kinds of fluids such as a gargle fluid and hand washing water. The apparatus also has a valve or a nozzle (what is called a faucet or a tap) having a discharge port at the tip thereof disposed on the upper portion of the sink for each fluid supply mechanism. The different kinds of fluids include, for example, chemicals such as soapy water, a disinfectant and a gargle fluid except for water and warm water for washing hands. Furthermore, there is also known an apparatus that can supply warm air in addition to those liquids.

However, in the above-mentioned apparatus, it is required, for each fluid supply mechanism, to manufacture a valve or a nozzle (a faucet) by using a casting process, for example, and also to mount them on the upper portion of the sink. The production of these parts costs a great deal and takes a lot of time, and it is a real bottleneck in attempting to reduce the manufacturing cost of the whole apparatus.

Furthermore, as a fluid supply apparatus for gargling and washing hands, there is known an apparatus provided with a common cover of a hollow covering member made of resin, for example, standing on the upper surface of the sink. In this kind of apparatus, a discharge port of each fluid supply mechanism is provided at a predetermined position of the common cover, instead of providing each fluid supply mechanism with what is called a faucet.

According to such a constitution, a supply tube of each fluid supply mechanism is connected to the corresponding discharge port in the cover, so that the need for providing each fluid supply mechanism with a faucet individually is eliminated.

However, in order to manufacture such a cover, it is required to prepare exclusive molding dies and to mold the cover by filling resin material into the exclusive molding dies. Also, it is required to prepare various types of molding dies in accordance with the type of fluid supply apparatus, since numbers and/or types of the discharge holes to be formed in the cover are changed. In addition, the design of the cover itself is sometimes changed in accordance with the type of fluid supply apparatus. Furthermore, in such a case, the covers are to be manufactured in small lots. Accordingly, the manufacturing cost including the expense for molding dies increases a great deal, and it is hard to achieve a successive cost reduction in comparison with the case where a faucet is provided individually for each fluid supply mechanism when they are manufactured in small lots.

Furthermore, such a cover is usually mounted upright on a sink along the periphery of a concavity or recess thereof. In the case of a prior art cover, since it is considerably large and high, it will cover a part of the recess when it is mounted upright on the sink. Thus, a part of the light from above is blocked by the cover, and the user has to suffer much inconvenience in using the fluid supply apparatus when he washes his hands since a part of the sink recess is darkened at his hands. Furthermore, such an arrangement is not preferable from the view of design and appearance of the apparatus since it gives the impression of being untidy at the periphery of the sink.

SUMMARY OF THE INVENTION

The present invention has been developed in view of above-mentioned technical problems. A purpose of the present invention is to provide a system and a method effective for prevention of infectious diseases. Another purpose of the present invention is to provide an apparatus for supplying fluids that preferably can be utilized suitably for the above-mentioned system.

Accordingly, a first aspect of the present invention provides a prevention system against infectious diseases, comprising: a fluid supply apparatus provided with a sink and a plurality of fluid supply mechanisms for supplying different kinds of fluids, having at least a hand washing function and a gargle supply function, and disposed near a doorway in a building. A human body detection sensor detects a person entering into the building from the doorway and a voice output apparatus outputs a vocal sound to recommend that the person conduct gargling and hand washing when the human body detection sensor detects him or her.

Also, a second aspect of the present invention provides a method of preventing infectious diseases, comprising the steps of: arranging a fluid supply apparatus near a doorway in a building, wherein the fluid supply apparatus is provided with a sink and a plurality of fluid supply mechanisms for supplying different kinds of fluids, and having at least a hand washing function and a gargle supply function; and outputting a vocal sound to recommend that a person conduct gargling and hand washing when he or she enters into the building from the doorway.

According to the first or the second aspect of the present invention, a person entering the building from a doorway is recommended to wash their hands and gargle by a voice, and the chemical supply apparatus A is provided near the doorway. Therefore, the person can wash his or her hands and gargle without feeling troubled. As a result, it is possible to effectively prevent infectious diseases. Allergy can also be prevented effectively.

Further, a third aspect of the present invention provides an apparatus for supplying fluids, and the apparatus includes a plurality of fluid supply mechanisms for supplying different kinds of fluids, and a discharge port of each fluid supply mechanism is provided in a predetermined portion of a common unit-body disposed on an upper portion of a sink. The unit-body is provided with a pipe-shaped body disposed generally along at least a part of the periphery of a recess in a sink, and a base pedestal of which at least a part is formed hollow. The unit-body (pipe-shaped body) is mounted on an upper surface of the sink at an outer side of the recess periphery through the base pedestal.

According to the third aspect of the present invention, a unit-body (pipe-shaped body) having a pipe-like shaped body is provided on a sink along at least a part of the periphery of the sink recess, so that the system is simple and compact, and an outer design of the apparatus exhibits a simple and clean image. Therefore, the apparatus can suitably be installed in a hall or the like of an ordinary household without feeling a sense of congruity. When the above-described infection prevention system is applied to an ordinary household, the chemical supply apparatus can preferably be used. Especially, the pipe-shaped body is mounted on the upper surface of the sink at an outer side from the periphery of the recess, and the pipe-shaped body does not cover a portion of the recess from the periphery thereof Therefore, unlike the prior art using a cover body, when a user washes his or her hands, the hands are not darkened, and the user's comfort is not hindered. Further, because the body is pipe-shaped, it is possible to use a commercial pipe material, and as compared with the conventional resin mold cover body, a producing-cost including mode can be reduced.

In the fluid supply apparatus, it is preferable that the plurality of fluid supply mechanisms include at least two fluid supply mechanisms for supplying hand washing water, warm water, soapy water, a disinfectant, a gargle fluid and warm air.

In this case, it is possible to preferably wash hands, or in addition to this, to gargle.

Further, in the above fluid supply apparatus, it is preferable that the plurality of fluid supply mechanisms include fluid supply mechanisms for supplying either one of hand washing water or warm water, soapy water and a disinfectant and a gargle fluid.

In this case, it is possible to wash hands, disinfect the hands hygienically, and to gargle. Therefore, the chemical supply apparatus can suitably be used as the chemical supply apparatus when the infection prevention system is applied.

Furthermore, in the above fluid supply apparatus, it is preferable that a detection sensor for detecting a user's operating motion to use a fluid of a discharge port of the unit-body is provided at a vicinity of the discharge port. By detecting the user's operating motion using the detection sensor, a fluid supply mechanism corresponding to the discharge port is driven, and the fluid is automatically supplied from the discharge port.

In this case, the fluid supply mechanism is driven to automatically supply the fluid from the discharge port. Therefore, it is unnecessary for users to touch the apparatus with their hands, and it is possible to wash and disinfect the hands more hygienically.

Furthermore, in the above fluid supply apparatus, it is preferable that the plurality of fluid supply mechanisms include at least a fluid supply mechanism for supplying a gargle, and the fluid supply apparatus is provided with a gargle discharge switch that is to be operated when the gargle is discharged from the discharge port.

In this case, it is possible to gargle in accordance with the will of the user. Therefore, the apparatus can preferably be used as the fluid supply apparatus when the infection prevention system of the invention is applied.

Furthermore, in the above fluid supply apparatus, it is preferable that a fluid supply mechanism for supplying a chemical, one of the plurality of fluid supply mechanisms, feeds the chemical from a chemical container to a corresponding discharge port, and the unit-body is provided with an alarm device for sounding an alarm when a remaining amount of the chemical in the chemical container is reduced below a predetermined level. In this case, it is possible to replenish the chemical, and to avoid a situation in which the remaining amount of chemical becomes zero and the chemical actually runs out.

Furthermore, in the above fluid supply apparatus, it is preferable that the base pedestal of the unit-body is made of synthetic resin and is formed generally U-shaped in cross section so that an upper side is opened. The pipe-shaped body supported on an upper surface of the base pedestal is made of metal and provided with a threaded hole at a predetermined portion in a lower part thereof, and is fastened to the base pedestal by tightening a screw member into the threaded hole from a bottom of the base pedestal. The base pedestal is fastened to the sink through metal washers and screw members disposed above and below the bottom plate of the base pedestal.

In this case, it is possible to easily and reliably mount the unit body having the resin base pedestal and the metal pipe body to the upper surface of the sink.

Furthermore, in the above fluid supply apparatus, it is preferable that basic constituent elements of each fluid supply mechanism except for each discharge port, and piping elements and electric wiring elements be placed inside the pipe-shaped body or the base pedestal so as to be accommodated in a single accommodation case, and the accommodation case is disposed at the vicinity of the sink.

In this case, the basic constituent elements of each fluid supply mechanism can be assembled separately from the assembling operation of the apparatus and can be accommodated in the single accommodation case, and the assembling work of each fluid supply mechanism is facilitated. The basic constituent elements of the assembled fluid supply mechanism can easily be moved together with the single accommodation case. Therefore, the assembling operation of the apparatus is facilitated, inspection and repair work at the time of maintenance is facilitated, and service is also enhanced. Further, even if the design of the sink is varied, the basic constituent elements of each fluid supply mechanism accommodated in the single accommodation case can commonly be used, and efficiency when various kinds of chemical supply apparatuses are produced can be enhanced.

Furthermore, in the above fluid supply apparatus, it is preferable that the sink is formed into the shape of a substantially rectangular parallelepiped. In this case, the chemical supply apparatus can agreeably be disposed in a hall of an ordinary household. Further, even when stone material (which adds a quality appearance to the sink and which is excellent in design) is used as material for the sink, it is easy to form its outer shape.

Furthermore, in the above fluid supply apparatus, it is preferable that the unit-body is divided into a plurality of unit-body pieces substantially along at least a part of a periphery of a recess of the sink. In this case, it is possible to enhance the flexibility of the layout of the unit body itself and the discharge port of each fluid supply mechanism.

Furthermore, a fourth aspect of the present invention provides a fluid supply apparatus including a plurality of fluid supply mechanisms for supplying different kinds of fluids, and discharge ports of the fluid supply mechanisms are disposed on an upper portion of a sink. A detection sensor for detecting a user's motion to use a fluid to be supplied by each discharge port of the unit-body is provided respectively at a vicinity of the discharge port. By detecting the user's operating motion using the detection sensor, a fluid supply mechanism corresponding to the discharge port is driven and the fluid is automatically supplied from the discharge port. A central detection sensor disposed at a position corresponding approximately to a center of the sink recess periphery far from a user of a sink is set such that a detecting direction points to approximately a center of the sink recess. The other detection sensors are set such that their detecting directions become estranged from the direction points to approximately a center of the sink recess to a closer direction to the user by a predetermined angle.

According to the fourth aspect of the present invention, when a user puts a hand with in the sensing range of the central detection sensor, other sensors can be prevented from erroneously detecting this motion. When the user puts a hand within the sensing range of another sensor, the central detection sensor can be prevented from erroneously detecting this motion.

In the fluid supply apparatus, it is preferable that the discharge port of each fluid supply mechanism is provided at a predetermined portion of a common unit-body, and the common unit-body is disposed on an upper portion of the sink. In this case, the above effect obtained by the above fluid supply apparatus according to the fourth aspect of the present invention can similarly be obtained in a fluid supply apparatus in which a discharge port of each fluid supply mechanism is provided on a predetermined portion of a common unit body, and the unit body is disposed on an upper portion of a sink.

DETAILED DESCRIPTION OF THE INVENTION

Preferred embodiments of the present invention will be described in detail below with reference to the accompanying drawings.

Figure 1:
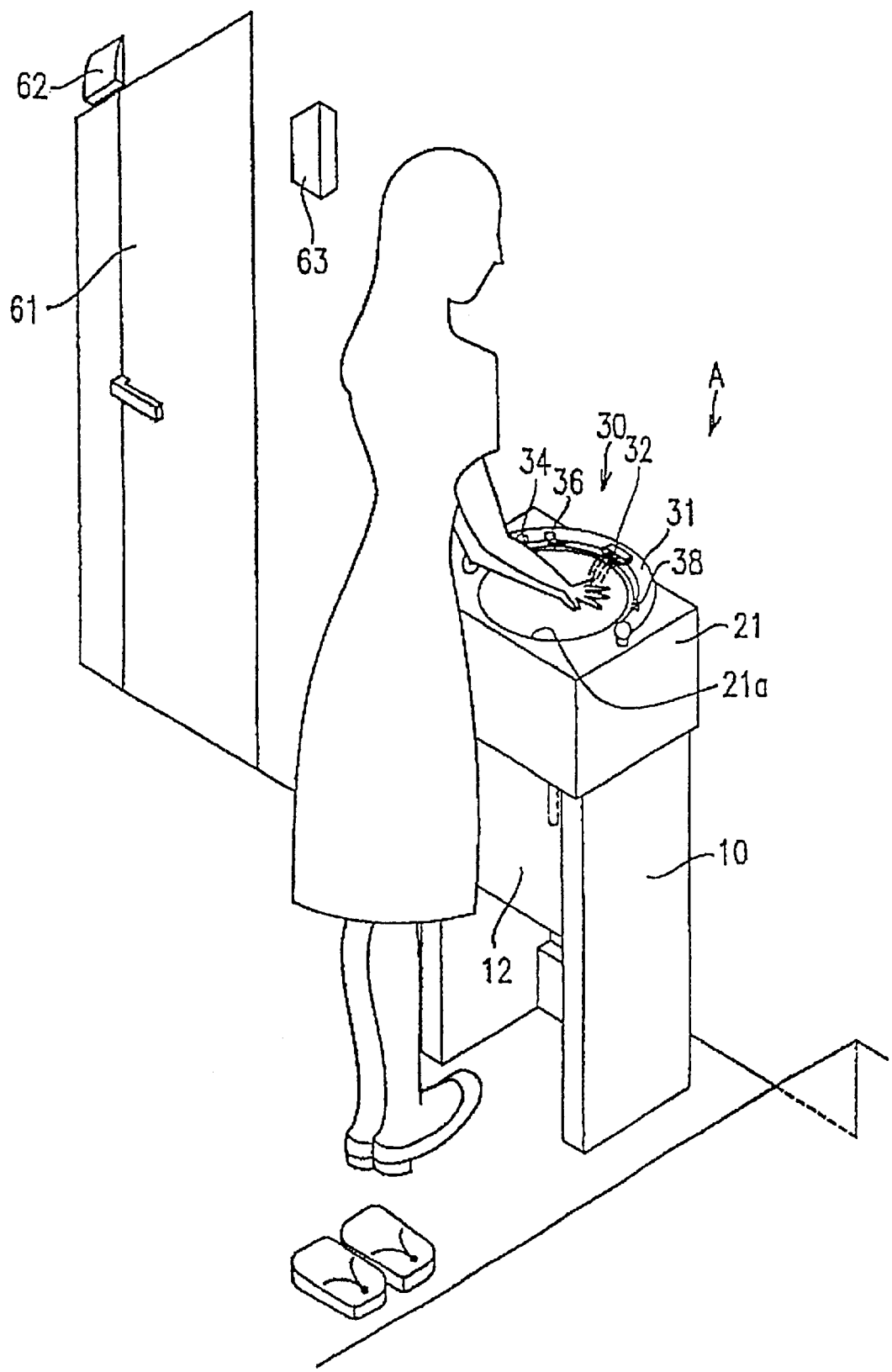
FIG. 1 is a schematic view showing a structure of one example of a prevention system for preventing infectious diseases according to an embodiment of the present invention.

FIG. 1 is a schematic view showing a structure of one example of a prevention system for preventing infectious diseases according to an embodiment of the invention. As shown in FIG. 1, in the infection prevention system of the embodiment, a chemical supply apparatus A for washing hands and gargling is installed on a floor near a doorway 61 of a hall of an ordinary household. The chemical supply apparatus A serves as a fluid supply apparatus for preventing infectious diseases. The chemical supply apparatus A corresponds to a "fluid supply apparatus" described in claims.

A human body detection sensor 62, such as an infrared radiation sensor, for detecting a human body utilizing infrared radiation is provided above the doorway 61 in the hall so as to detect a person (i.e., a homeowner or visitor) entering home from outside.

Further, a voice output apparatus 63 is provided near the doorway 61. When a person entering the home is detected by the human body detection sensor 62, the voice output apparatus 63 outputs a preset voice to the person. In the voice output apparatus 63, a voice recommends that the person wash hands and gargle. For example, a voice "Welcome home, wash your hands and gargle" of elementary school child of about fifth to sixth grade is previously set so as to prevent infectious diseases.

As described above, the chemical supply apparatus A is provided near the doorway of the building and the voice output apparatus 63 outputs words recommending washing of hands and gargling to a person entering the building from the doorway by means of voice. Therefore, the person can wash his or her hands and gargle without feeling troublesomeness. As a result, it is possible to effectively prevent infectious diseases. Allergy can also be prevented effectively.

Figure 2:
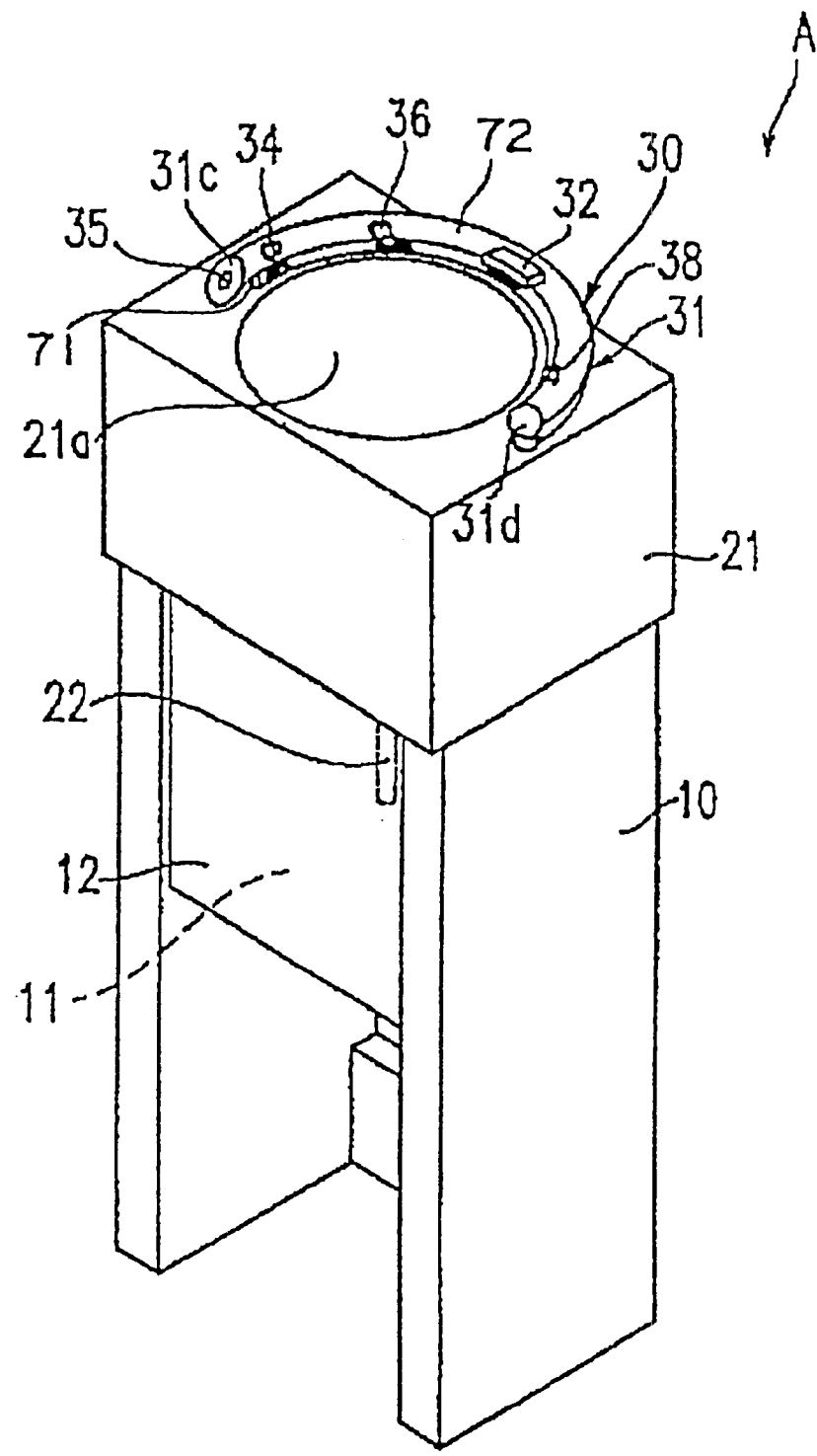
FIG. 2 a schematic perspective view showing one example of a chemical supply apparatus used in the above prevention system for preventing infectious diseases.
Figure 3:
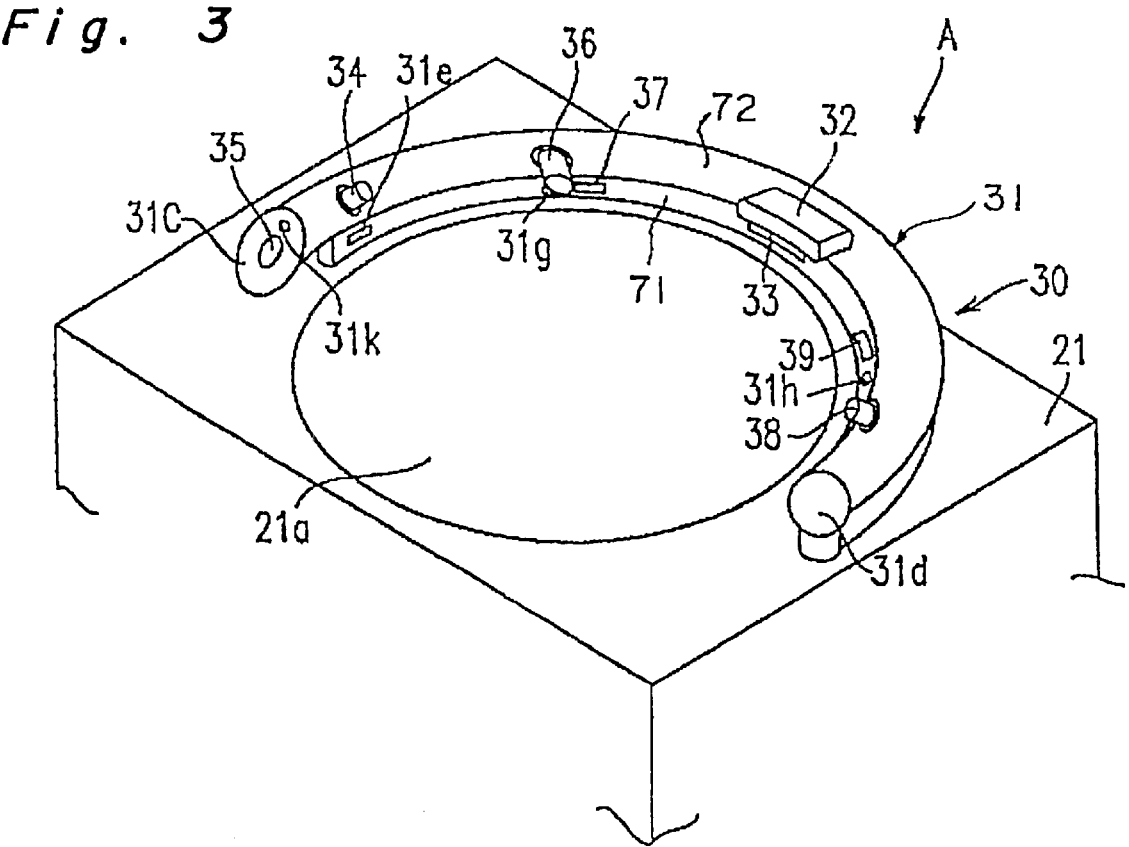
FIG. 3 is an enlarged perspective view of an upper portion of the chemical supply apparatus.
Figure 4:
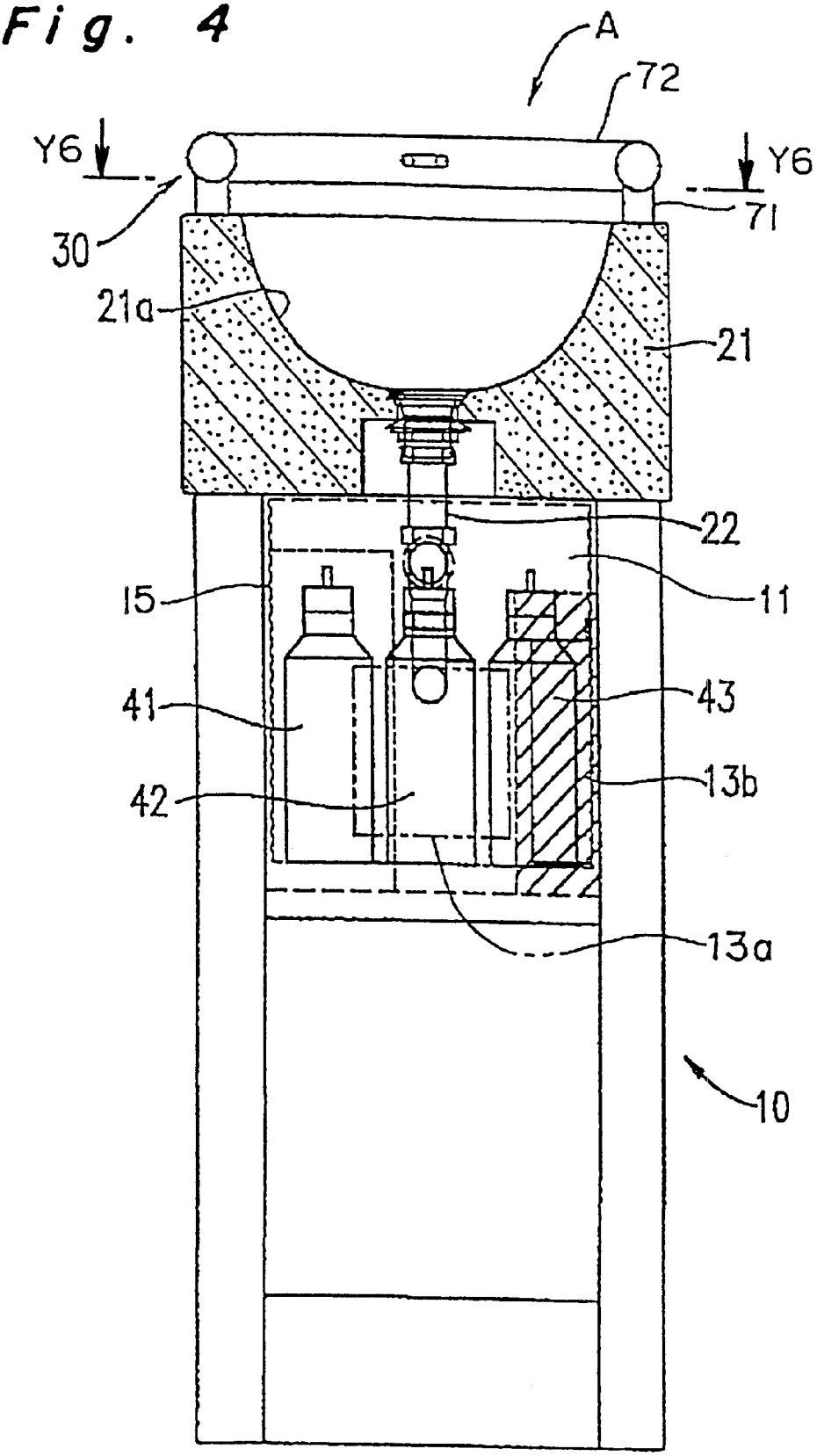
FIG. 4 is an explanatory front view of the chemical supply apparatus.
Figure 5:
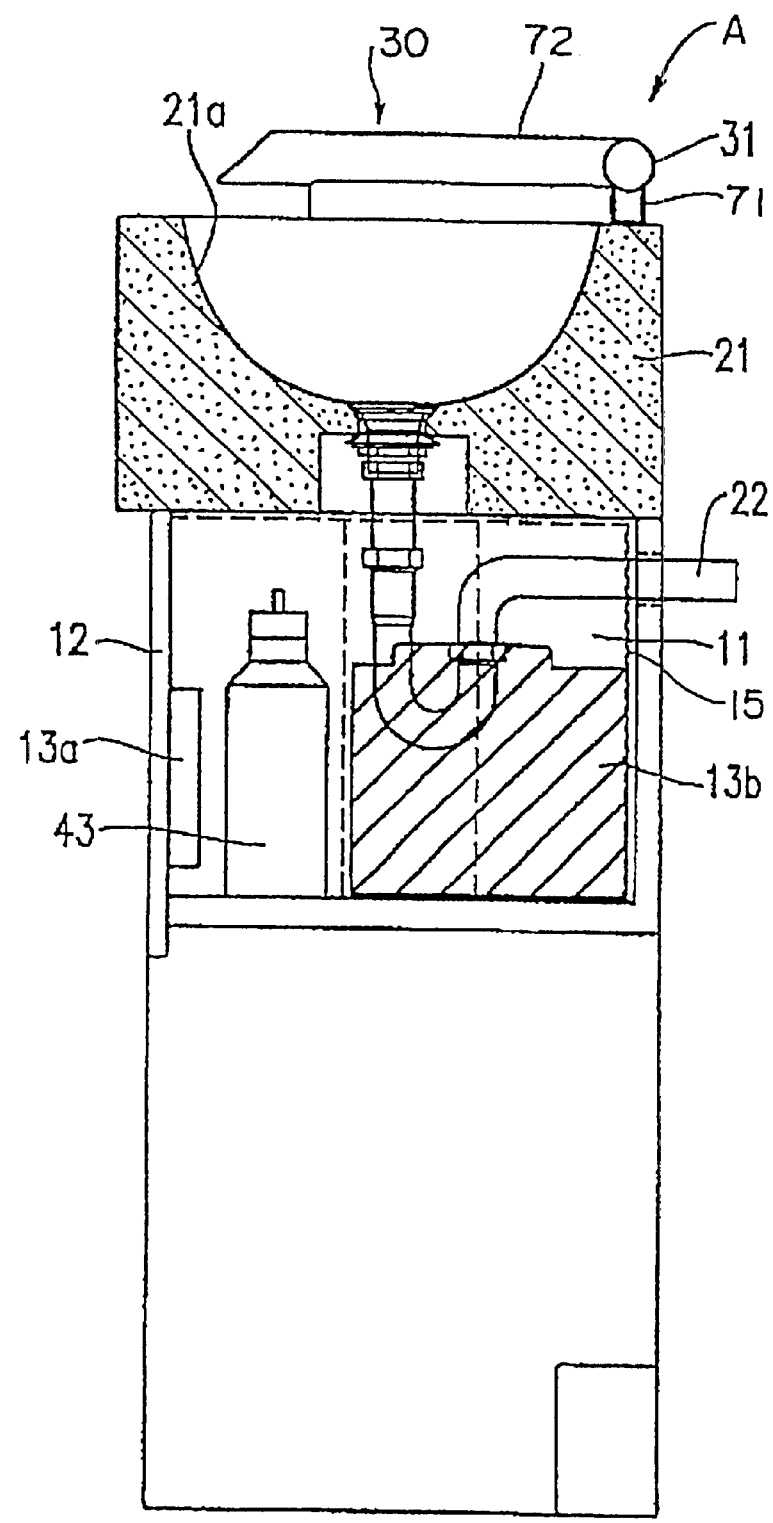
FIG. 5 is an explanatory side view of the chemical supply apparatus.

FIG. 2 is a schematic perspective view showing one example of the chemical supply apparatus used in the above infection prevention system. FIG. 3 is an enlarged perspective view of an upper portion of the chemical supply apparatus. FIG. 4 is an explanatory front view of the chemical supply apparatus. FIG. 5 is an explanatory side view of the chemical supply apparatus.

As shown in these drawings, the chemical supply apparatus A includes a sink 21 mounted on a support stand 10, and a nozzle unit 30 is disposed on the sink 21. The chemical supply apparatus A is placed along a wall surface near the doorway 61 of the hall.

The sink 21 is made of stone material, for example, and is formed into a rectangular solid shape. In other words, the sink 21 has the shape of a substantially rectangular parallelepiped. The sink 21 is provided therein with a substantially semi-spherical recess 21a whose upper portion is opened.

Since the sink 21 is formed into the rectangular solid shape, the chemical supply apparatus A can agreeably be disposed in a hall of an ordinary household. Further, even if stone material which adds a quality appearance to the sink 21 and which is excellent in design is used as material for the sink 21, it is easy to form its outer shape.

As can be seen in FIG. 5, an upper end of a water pipe 22 is connected to a lower portion of the sink 21, and an interior of the recess 21a and the water pipe 22 communicate with each other. The water pipe 22 is bent into a U-shape in an accommodation chamber 11 provided in an upper portion of the support stand 10. The water pipe 22 extends horizontally from the back side of chamber 11, and is connected to a discharge pipe (not shown) provided inside a wall surface in front of which the chemical supply apparatus A is disposed.

When the discharge pipe is provided under the floor, the water pipe 22 is connected to the discharge pipe under the floor.

A pipe-shaped unit body 30 (nozzle unit) is provided on an upper surface of the sink 21. The unit body 30 is bent into a substantially arc shape along a peripheral edge of an opening of the recess 21a. The nozzle unit 30 has a hollow casing 31 (unit casing) which is formed into an arc shape along substantially half of a periphery of the opening of the recess 21a on the back thereof. The casing 31 has a circular hollow pipe-shaped body 72 and a base pedestal 71 disposed in a lower portion of the pipe body 72.

More preferably, the pipe-shaped body 72 is made of commercial pipe material (e.g., stainless steel pipe material), the base pedestal 71 is made of synthetic resin, and its cross section profile is rectangular for example, and at least a part thereof is hollow. The pipe body 72 is mounted on the upper surface of the sink 21 at the outer side of the periphery of the opening of the recess 21a through the base pedestal 71.

The nozzle unit 30 is provided along at least a part of the periphery of the recess 21a of the sink 21, and the nozzle unit 30 has the casing 31 with the pipe-like shape. Therefore, the system is simple and compact, and an outer design of the apparatus exhibits a simple and clean image. Therefore, the apparatus can agreeably be installed in a hall or the like of an ordinary household. When the above-described infection prevention system is applied to an ordinary household, the chemical supply apparatus A can suitably be used.

The pipe-shaped body 72 is mounted on the upper surface of the sink 21 at the outer side of the periphery of the recess 21a, and the pipe body 72 does not cover a portion of the recess 21a from the periphery thereof. Therefore, unlike the prior art apparatuses using a cover body, when a user washes his or her hands, the hands are not darkened, and the user's comfort is not hindered. Further, the body 72 of the unit casing 31 has a pipe-like shape, so it is possible to use a commercial pipe material, and as compared with the conventional resin mold cover body, a producing cost including molding dies can be reduced.

Figure 6:
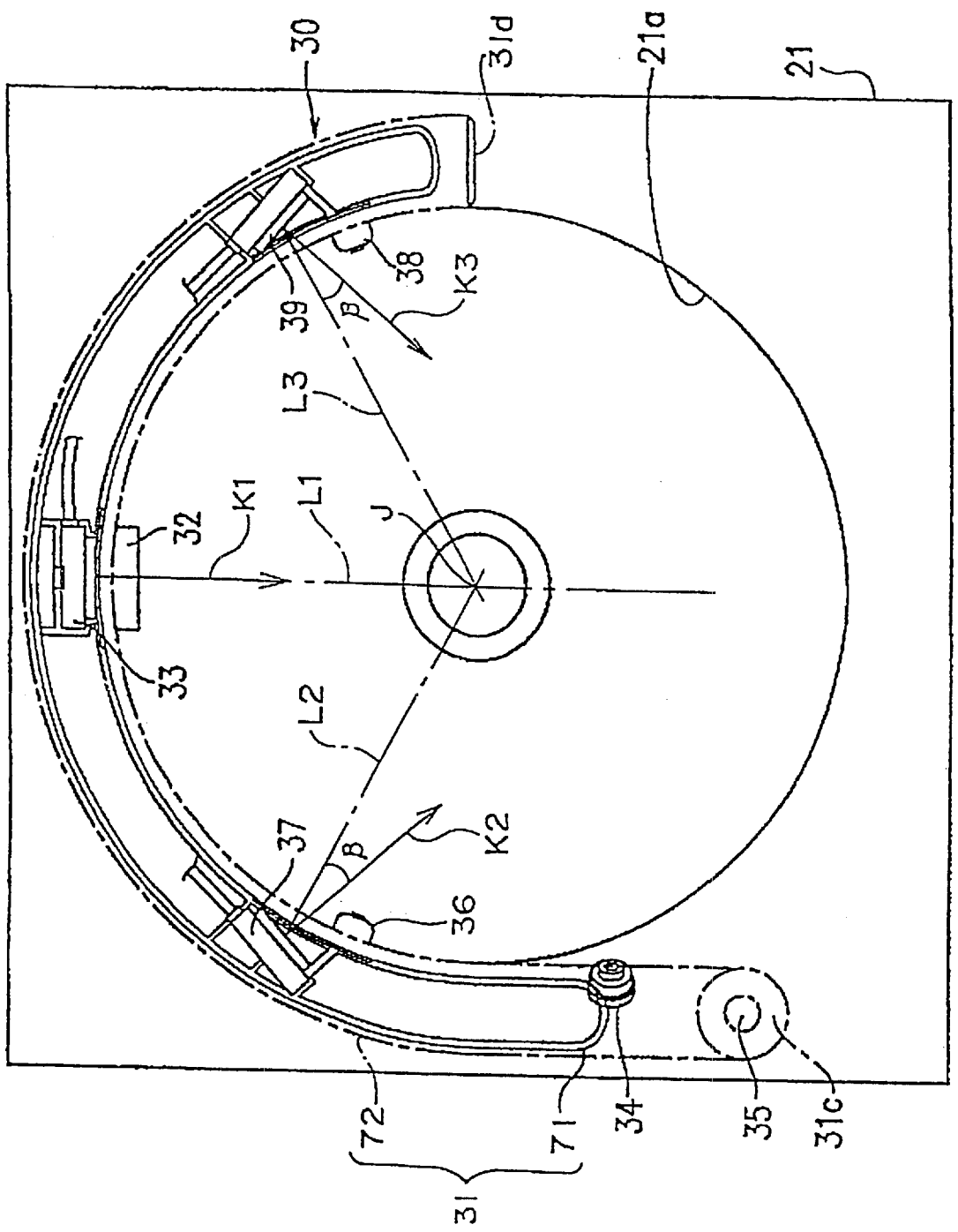
FIG. 6 is an explanatory plan view taken along a line Y6—Y6 in FIG. 4.

FIG. 6 is an explanatory plan view taken along line Y6—Y6 in FIG. 4. As can be seen in FIGS. 6 and 3, one end portion of the base pedestal 71 extends straight toward a front surface, and a pipe body portion located on the end portion of the base pedestal 71 extends straight closer to the front surface than the end portion of the base pedestal 71. An end surface 31c of the end portion of the pipe body 72 that extends straight is an inclined surface. It is inclined by a predetermined angle with respect to a vertical surface that is parallel to the front surface. The other end surface 31d of the pipe body 72 is a vertical surface which is vertical in the upper and lower direction.

As shown in FIGS. 3 and 6, a water supply nozzle (for a first fluid supply mechanism) 32 is disposed at a portion of the pipe body 72 located on a back surface side of the sink 21 (i.e., a substantially central portion of the pipe body 72). The water supply nozzle 32 extends toward the front surface by a predetermined amount. A cross section of the water supply nozzle 32 has an oblong figure shape in the lateral direction. The water supply nozzle 32 is connected to a water supply pipe 55 (see FIG. 8) provided on an accommodating portion 11 on the upper portion of the support stand 10 through a water supply solenoid valve 56 (see FIG. 8).

A water supply sensor 33 is provided at a portion of the base pedestal 71 located below the water supply nozzle 32 (i.e., a substantially central portion of the base pedestal 71). The water supply sensor 33 comprises an approaching switch (non-contact switch) utilizing infrared radiation. When a user needs water and his or her fingers approach the water supply sensor 33, this action is detected by the water supply sensor 33.

A substantially columnar shaped gargle nozzle (for a second fluid supply mechanism) 34 for discharging gargle fluid is provided in the vicinity of the inclined surface 31c of the pipe body 72. The gargle nozzle 34 projects by a predetermined amount in an upward direction relative to the recess 21a from the pipe body 72 in a slightly oblique manner.

The gargle fluid from a gargle bottle 41 (see FIG. 4) accommodated in the accommodating portion 11 of the support stand 10 is diluted into about 80 to 100 times with water supplied from the water supply pipe 55 (see FIG. 8) through a gargle water supply solenoid valve 56 (see FIG. 8), and the diluted gargle fluid with water is discharged from the gargle nozzle 34 in a jet.

The gargle nozzle 34 has a basic structure similar to that disclosed in Japanese Patent No. 2567573, for example. Water is supplied from the water supply pipe 55 through a predetermined space. The gargle fluid in the gargle bottle 41 is pumped and supplied through a gargle solenoid valve 53 (see FIG. 7) by vacuum generated when water is discharged from the gargle nozzle 34. The gargle fluid and water are mixed by the gargle nozzle 34 in this manner, and the gargle fluid is discharged in jet.

The base pedestal 71 is provided at its portion below the gargle nozzle 34 with a discharge port 31e for discharging excessive water supplied to the gargle nozzle 34.

A gargle discharge switch 35 is disposed on the inclined surface 31c of the pipe body 72 (inclined surface near the gargle nozzle 34). The gargle discharge switch 35 is to be operated in order for the gargle to be discharged from the gargle nozzle 34 in jet. A gargle-out lamp 31k is disposed above the gargle discharge switch 35, and indicates when gargle reserved in the gargle bottle 41 is out.

Further, a substantially columnar soapy water nozzle (for a third fluid supply mechanism) 36 is disposed at a substantially intermediate portion of the pipe body 72 between the gargle nozzle 34 and the water supply nozzle 32. The soapy water nozzle 36 projects by a predetermined amount toward the sink recess 21a slightly obliquely from the pipe body 72. The soapy water nozzle 36 discharges soapy water stored in a soapy water bottle 42 (see FIG. 4) accommodated in the accommodating portion 11 of the support stand 10.

The base pedestal 71 is provided with a soapy water-out lamp 31g below the soapy water nozzle 36, and the soapy water-out lamp 31g indicates when the soapy water is out. A soapy water discharge sensor 37 is provided on the side of the soapy water-out lamp 31g. The soapy water discharge sensor 37 comprises an approaching switch (non-contact switch) utilizing infrared radiation. When a user intends to use the soapy water and his or her hand approaches the soapy water discharge sensor 37, the sensor 37 detects the hand.

A substantially columnar disinfectant nozzle (for a fourth fluid supply mechanism) 38 is provided near a vertical end 31d of the pipe body 72 (end opposite from the inclined surface 31c having the gargle nozzle 34). The disinfectant nozzle 38 projects by a predetermined amount toward the sink recess 21a slightly obliquely from the pipe body 72. The disinfectant nozzle 38 discharges disinfectant from a disinfectant bottle 43 (see FIG. 3) accommodated in an accommodating portion 11 of the support stand 10.

A disinfectant-out lamp 31h is provided on a portion of the base pedestal 71 located below the disinfectant nozzle 38. The disinfectant-out lamp 31h indicates when the disinfectant in the disinfectant bottle 43 is out. A disinfectant discharge sensor 39 is provided on the side of the disinfectant-out lamp 31h. The disinfectant discharge sensor 39 includes an approaching switch (non-contact switch) utilizing infrared radiation, for example. When a user intends to use disinfectant, and his or her hand approaches the disinfectant discharge sensor 39, the sensor 39 detects the hand.

As described above, the water supply sensor 33, the soapy water discharge sensor 37 and the disinfectant discharge sensor 39 are respectively provided near the water supply nozzle 32, the soapy water nozzle 36 and the disinfectant nozzle 38 for detecting the user's operating motion with respect to the chemical discharged from the nozzles. The sensors detect the user's operating motion, and the fluid supply mechanism (i.e., the first, second, third or fourth fluid supply mechanism) corresponding to that nozzle is driven so that the chemical is automatically supplied from the nozzle. Each fluid supply mechanism includes the storage tank, pump, and piping for supplying the particular chemical through the nozzle.

In the chemical supply apparatus A, the water supply sensor 33 of the above sensors is located at a portion of the sink recess 21a corresponding to a substantially central portion of the peripheral edge far from the user (left side in FIG. 6). The other soapy water discharge sensor 37 and the disinfectant discharge sensor 39 are respectively located at predetermined distances leftward and rightward from the water supply sensor 33 along the periphery of the sink recess 21a. The water supply sensor 33 corresponds to a "central detection sensor", and the soapy water discharge sensor 37 and the disinfectant discharge sensor 39 correspond to "other detection sensor".

As clearly seen in FIG. 6, in the present embodiment, a sensor surface of the central water supply sensor 33 is disposed substantially parallel to a tangent of the periphery of the sink recess 21a, and the soapy water discharge sensor 37 and the disinfectant discharge sensor 39 located at left and right sides are disposed so as to be inclined through predetermined angles with respect to the tangent direction of the periphery of the sink recess 21a.

That is, a sensing direction (see a solid arrow K1) of the water supply sensor 33 is set to point to a center J of the sink 21a (see a chain line L1). On the other hand, the sensing directions of the soapy water discharge sensor 37 and the disinfectant discharge sensor 39 are set to point in a direction away from a direction (see chain lines L2 and L3) that points to the center J of the sink recess 21a and instead points toward the user by a predetermined angle β (see solid lines K2 and K3).

If not only the center water supply sensor 33, but also the soapy water discharge sensor 37 and the disinfectant discharge sensor 39 are set such that their sensing directions are directed toward the center J of the sink recess 21a (see chain lines L2 and L3), when a user moved his or her hands forward of the water supply sensor 33 to use the water supply nozzle 32 (or when the hand approached), the soapy water discharge sensor 37 and/or the disinfectant discharge sensor 39 located at left and right sides would erroneously sense the user's hands, depending upon the approaching direction or its position. Thus, there is an adverse possibility that soapy water and/or disinfectant is inadvertently discharged from the soapy water nozzle 36 and/or the disinfectant nozzle 38. On the contrary, when the user moved his or her hand within the sensing region of the soapy water discharge sensor 37 or the disinfectant discharge sensor 39 to use the soapy water nozzle 36 or the disinfectant nozzle 38, the center water supply sensor 33 may erroneously sense the movement.

Such erroneous sensing is prone to be generated if the sensing ability of the soapy water discharge sensor 37 or the disinfectant discharge sensor 39 is higher, or if the sensing distance is shorter. When the peripheral shape of the sink recess 21a is circle, or when the sink recess 21a is small, such phenomenon is prone to be generated.

In the present embodiment, the sensing direction (see the solid arrow K1) of the center water supply sensor 33 is set to point to the center J of the sink recess 21a, and the water supply sensor 33 senses the hand of the user in the direction of the solid arrow K1. The sensing directions of the soapy water discharge sensor 37 and the disinfectant discharge sensor 39 are set to point in the sensing directions (see the solid arrows K2 and K3) in a direction that points toward the user through the predetermined angles β from the direction (see the chain lines L2 and L3) directed to the center J of the sink recess 21a. The soapy water discharge sensor 37 and the disinfectant discharge sensor 39 sense the user's hand in the directions of the solid arrows K2 and K3 offset from the direction of the solid arrow K1 toward the user (i.e., in a direction away from the center water supply sensor 33).

Therefore, when the user puts his or her hand into the sensing range of the center water supply sensor 33 to use the water supply nozzle 32, the left and right soapy water discharge sensor 37 and/or the disinfectant discharge sensor 39 are effectively prevented from erroneously sensing the hand. On the other hand, when the user puts his or her hand into the sensing range of the soapy water discharge sensor 37 or the disinfectant discharge sensor 39, the center water supply sensor 33 is effectively prevented from erroneously sensing the hand.

The above-described setting of the sensing direction of each of the detecting sensors when a plurality of detection sensors are provided is effective not only when the discharge nozzles (and corresponding detection sensors) are provided on the common unit like this embodiment, but also when the discharge nozzles (and detection sensors) are respectively provided independently.

As described above, the chemical supply apparatus A supplies hand-washing water, soapy water, disinfectant and gargle fluid. Thus, it is possible to wash hands, disinfect the hands and gargle hygienically. Therefore, the chemical supply apparatus A can suitably be used as a chemical supply apparatus when the infection prevention system is applied.

The detection sensors 33, 37 and 39 provided near the discharge nozzles 32, 36 and 38 of the nozzle unit 30 sense a user's operating motion with respect to the fluid of the discharge nozzle, and the fluid is automatically supplied from the discharge nozzle. Thus, when the user washes or disinfects his or her hands, it is unnecessary to touch the apparatus A with his or her hands, and it is possible to hygienically wash and/or disinfect his or her hands.

In this case, when the gargle fluid is discharged from the gargle nozzle 34, since the discharge switch 35 is provided, it is possible to gargle in accordance with a user's will. Therefore, this apparatus A can suitably be used as the chemical supply apparatus when the infection prevention system is applied.

Next, a structure of the unit casing 31 of the nozzle unit 30 and a mounting structure of the unit casing 31 to the sink 21 will be explained with reference to FIGS. 9 to 22.

Figure 9:
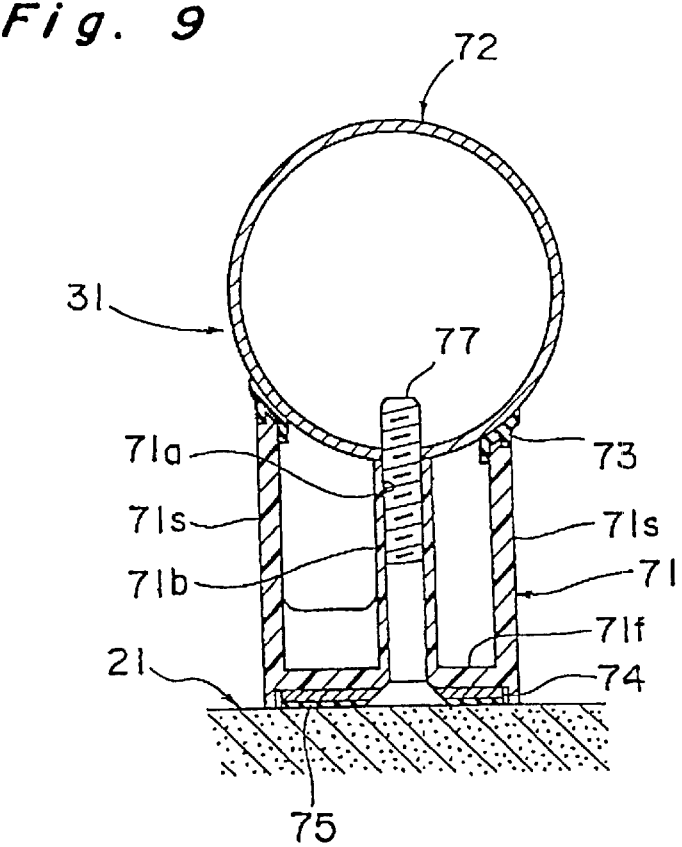
FIG. 9 is an explanatory vertical view of a unit casing showing a fixing structure of a pipe body of the unit casing to a base pedestal.
Figure 10:
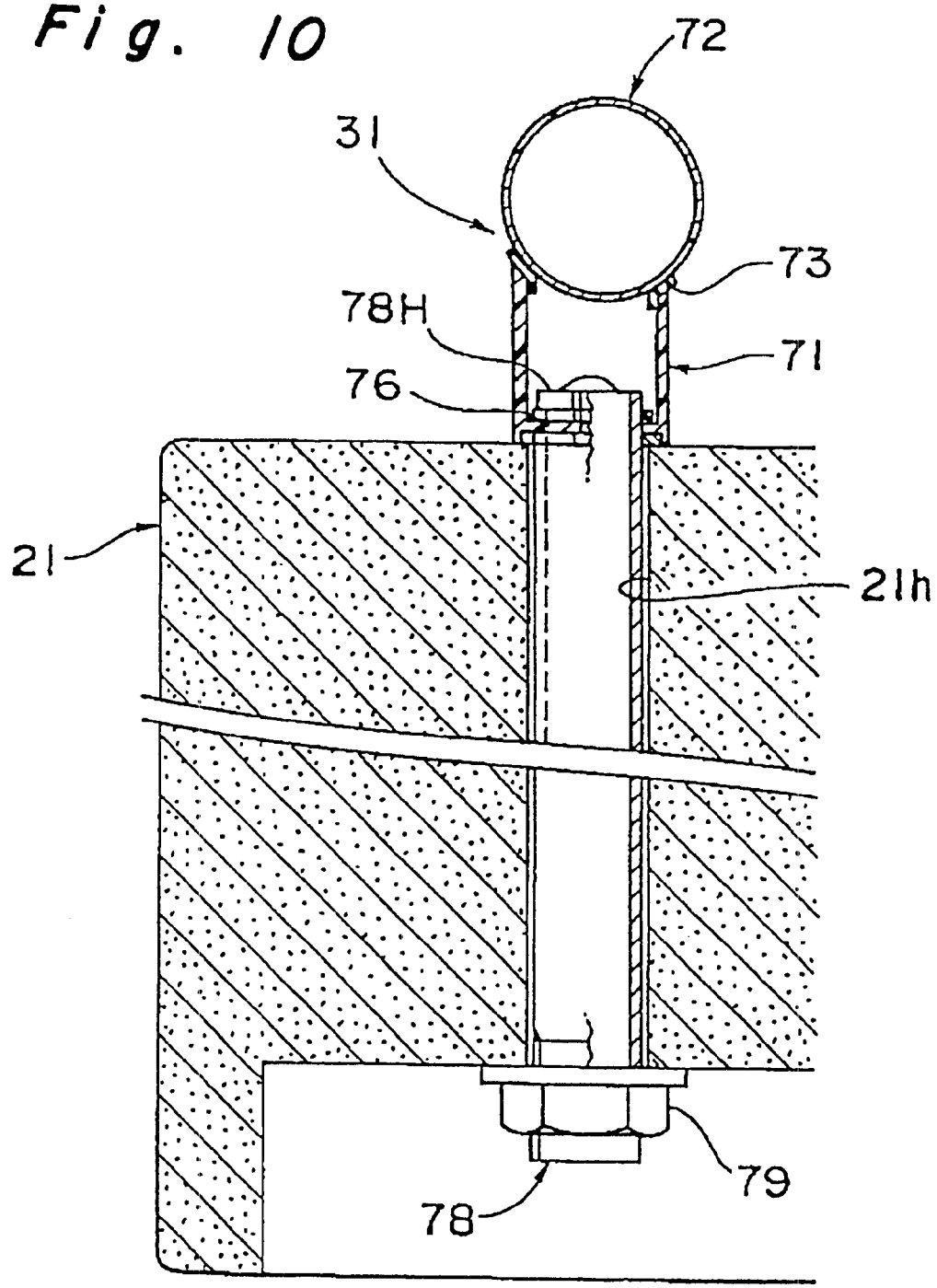
FIG. 10 is a partial explanatory vertical sectional view showing a fixing structure of the base pedestal to a sink.
Figure 11:
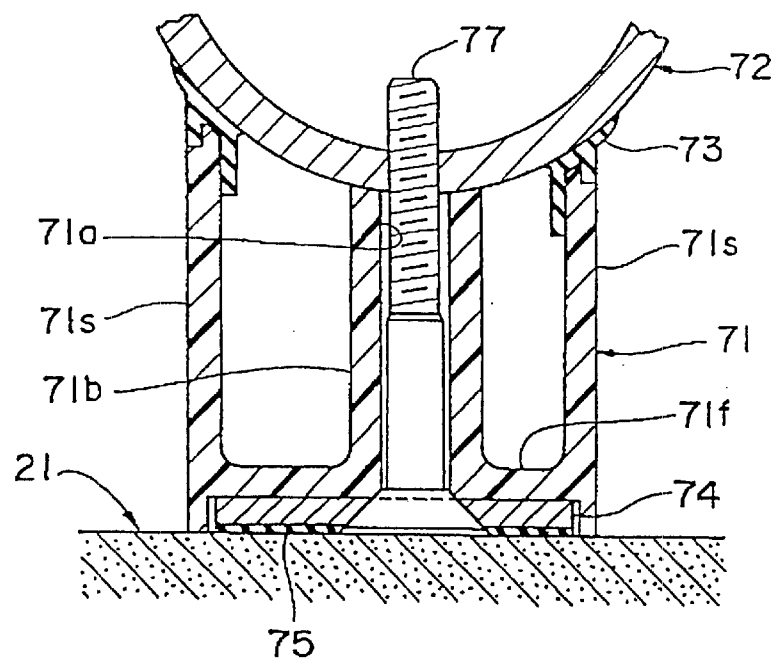
FIG. 11 is an enlarged explanatory sectional view of an essential portion in FIG. 9.
Figure 12:
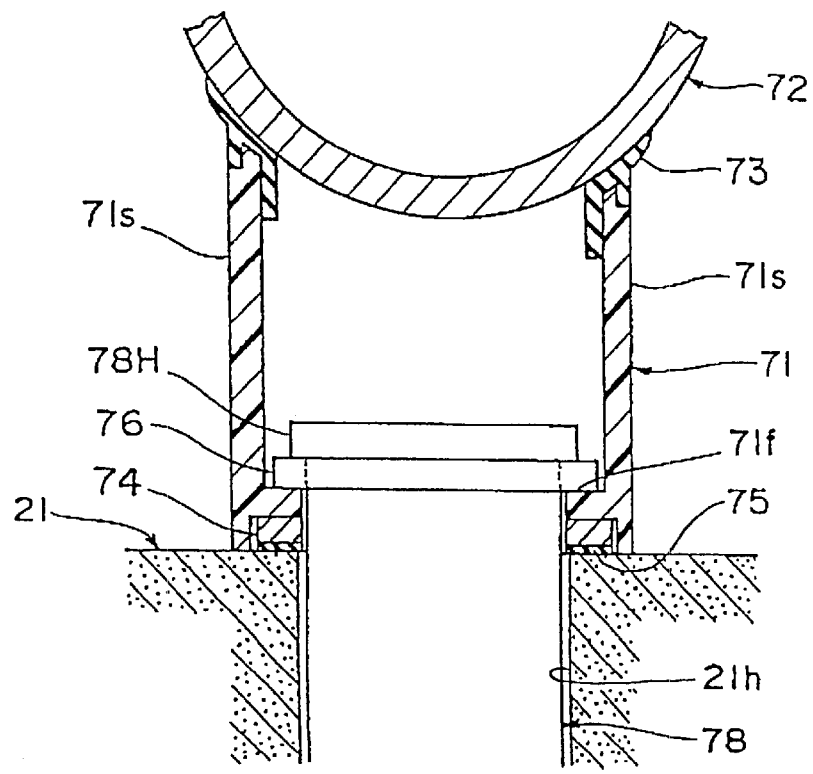
FIG. 12 is an enlarged explanatory sectional view of an essential portion in FIG. 10.

FIG. 9 is an explanatory vertical view of the unit casing 31 showing a fixing structure of the pipe body 72 of the unit casing 31 to the base pedestal 71. FIG. 11 is an enlarged explanatory sectional view of an essential portion of the unit casing 31. FIG. 10 is a partial explanatory sectional view showing a fixing structure of the base pedestal 71 to the sink 21. FIG. 12 is an enlarged explanatory sectional view of an essential portion of the fixing structure.

Figure 13:
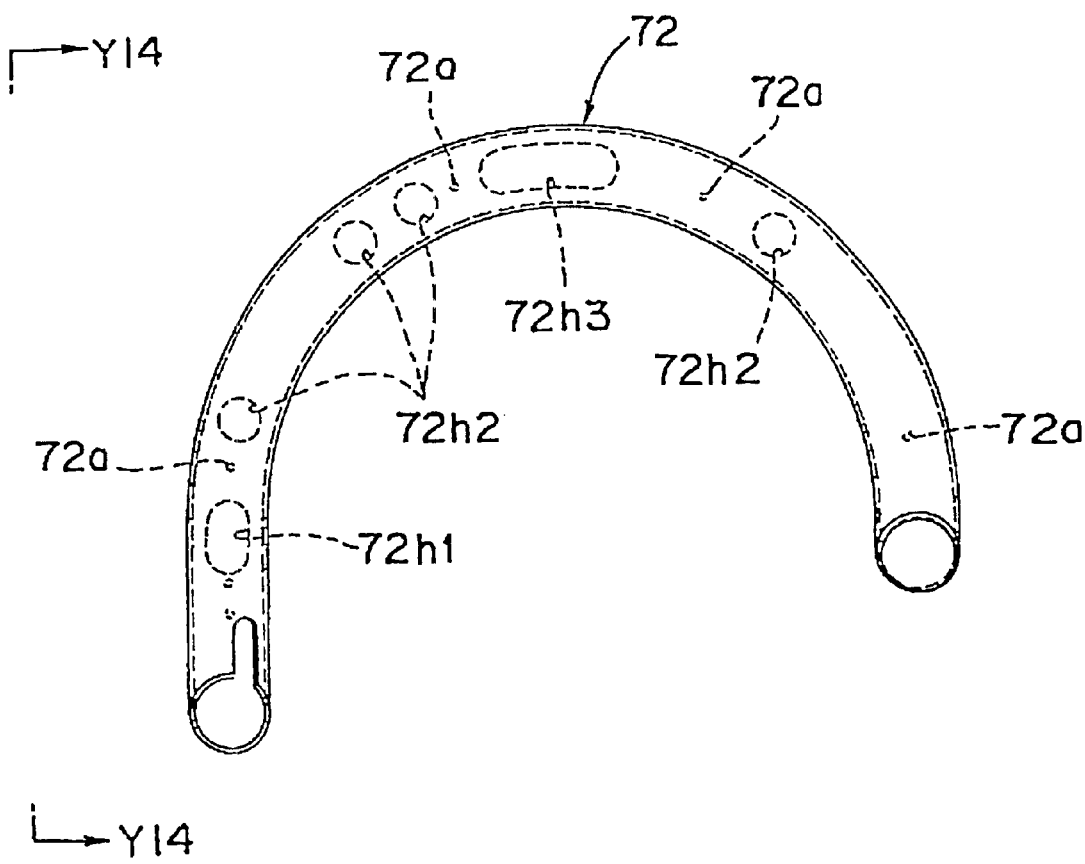
FIG. 13 is an explanatory plan view of the pipe body of the unit casing.
Figure 14:
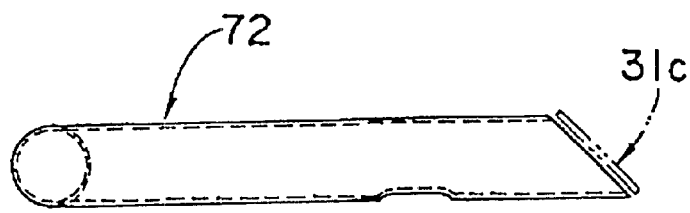
FIG. 14 is an explanatory side view of the pipe body, and is a view from an arrow Y14—Y14 in FIG. 13.

FIGS. 13 and 14 are respectively an explanatory plan view and an explanatory side view (as viewed from an arrow Y14—Y14 in FIG. 13) of the pipe body 72 of the unit casing 31. As shown in FIGS. 13 and 14, a lower surface of the pipe body 72 is provided with a large number of holes 72h1 to 72h3 through which pipes of the nozzles and electric wires of the sensors or chemical-out display lamps are pulled into the pipe body 72. A plurality of (e.g., four in this embodiment) threaded holes 72a are also formed in the lower surface of the pipe body 72 through which a screw member 77 (so called flat countersunk head screw, see FIGS. 9 and 11) is threadedly inserted.

Figure 18:
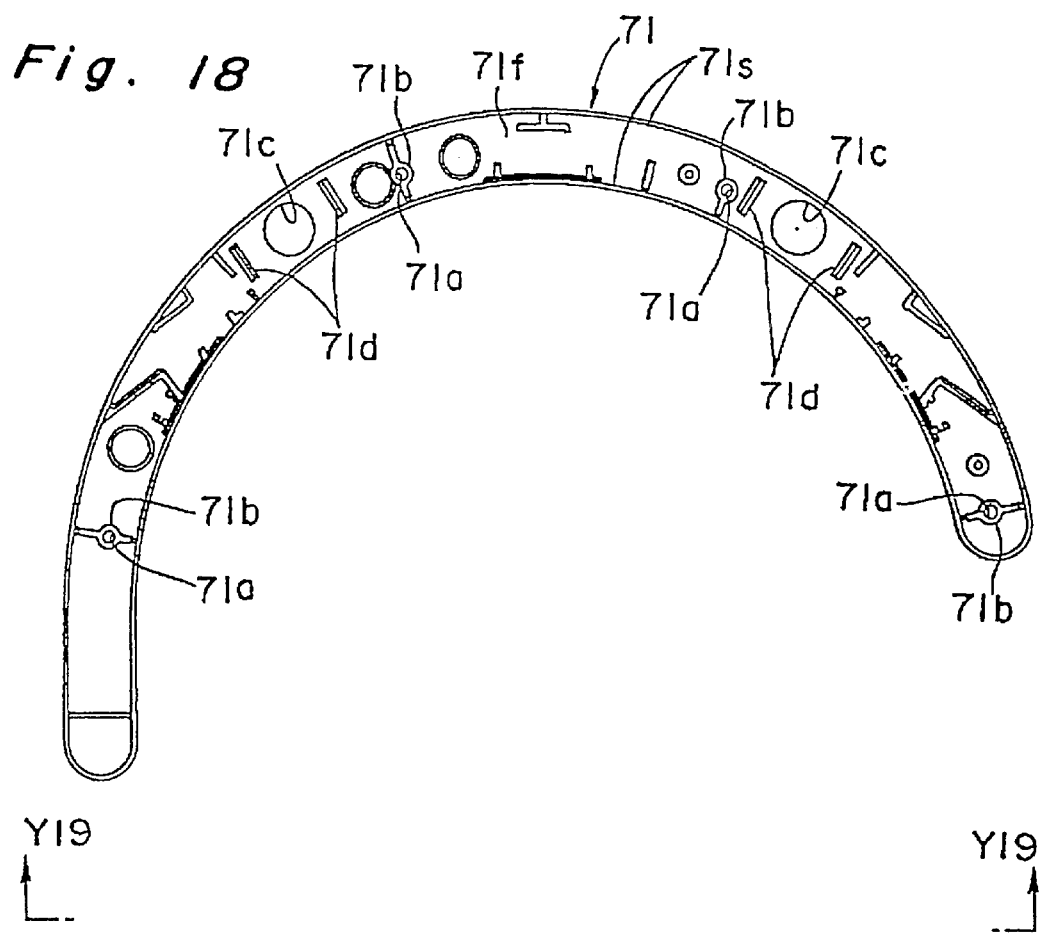
FIG. 18 is an explanatory plan view of the base pedestal of the unit casing.
Figure 19:
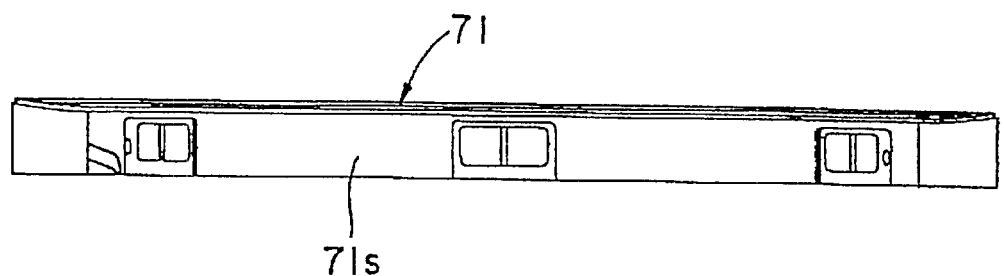
FIG. 19 is an explanatory front view of the base pedestal as viewed from a direction of an arrow Y19—Y19 in FIG. 18.

Further, FIGS. 18 and 19 are respectively an explanatory plan view and an explanatory front view (as viewed from an arrow Y19—Y19 in FIG. 18) of the base pedestal 71 of the unit casing 31. As shown in FIGS. 18 and 19, a boss 71b of the base pedestal 71 is formed at its portion corresponding to each of the threaded holes 72a with bosses 71b through which the screw portions 72a are inserted.

Further, a bottom plate 71f of the base pedestal 71 is provided with a plurality of bolt insertion holes 71c (two in this embodiment) through which the bolt members 78 (see FIGS. 10 and 12) are inserted.

Figure 20:
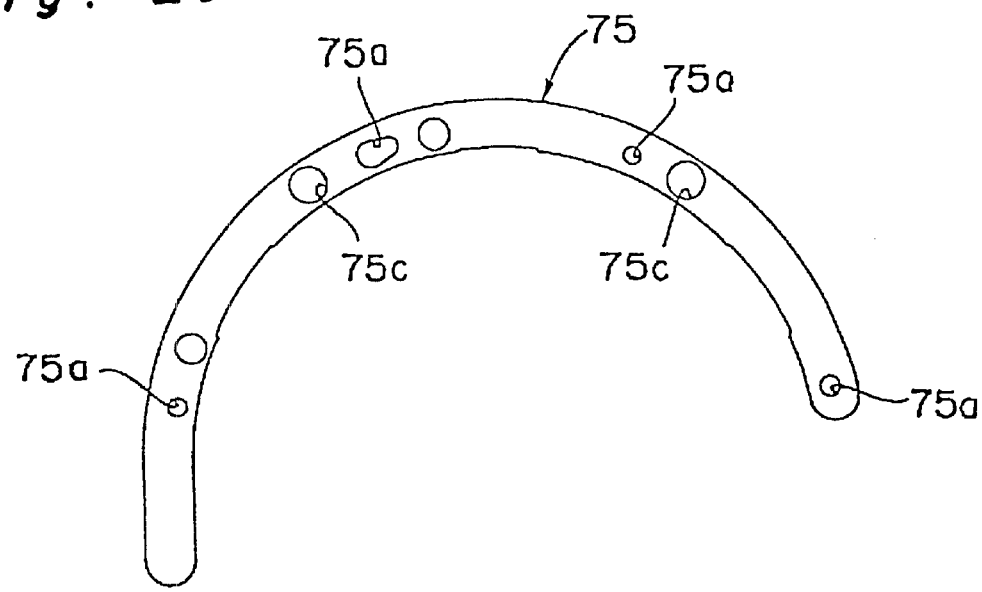
FIG. 20 is an explanatory plan view of a base packing and a base plate disposed below a bottom surface of the base pedestal.
Figure 21:
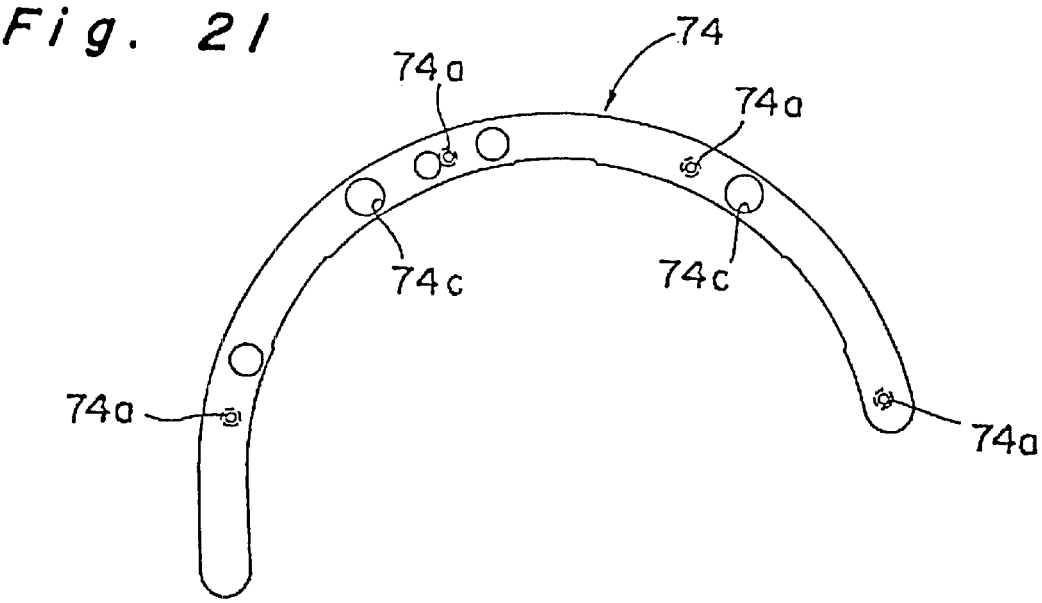
FIG. 21 is an explanatory plan view of the base plate disposed above the base packing.

FIGS. 20 and 21 are explanatory plan views of a base packing 75 and a base plate 74 disposed below the bottom plate 71f of the base pedestal 71. As shown in FIGS. 20 and 21, the base packing 75 and the base plate 74 are respectively provided with screw insertion holes 75a and 74a respectively corresponding to the screw insertion holes 71a of the base pedestal 71. Bolt insertion holes 75c and 74c, respectively, corresponding to the bolt insertion holes 71c of the base pedestal 71 are provided so that the bolt members 78 are inserted therethrough.

Figure 15:
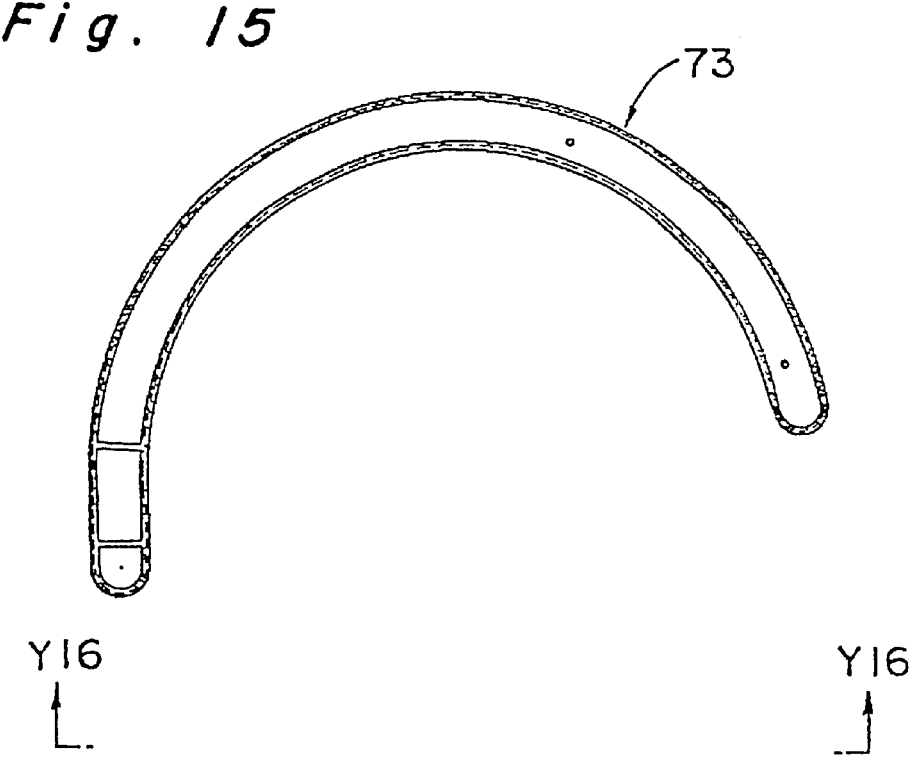
FIG. 15 is an explanatory plan view of a seal member mounted to the unit casing.
Figure 16:
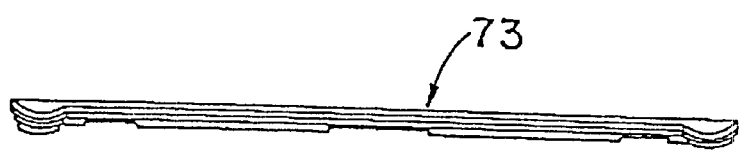
FIG. 16 is an explanatory front view of the seal member from a direction of an arrow Y16—Y16 in FIG. 15.
Figure 17:
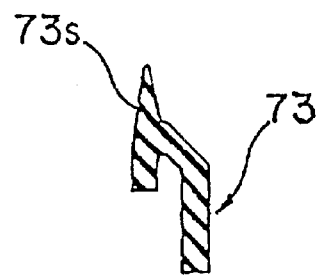
FIG. 17 is an enlarged sectional view of a tip end seat of the seal member.

A seal member 73 (see FIGS. 9 to 12) is provided between the pipe body 72 and an upper end of a side wall 71s of the base pedestal 71. FIGS. 15 and 16 are, respectively, an explanatory plan view and an explanatory front view (as viewed from a direction of an arrow Y16—Y16 in FIG. 15) of the seal member 73. FIG. 17 is an enlarged sectional view of a tip end seal 73s of the seal member 73.

Figure 22:
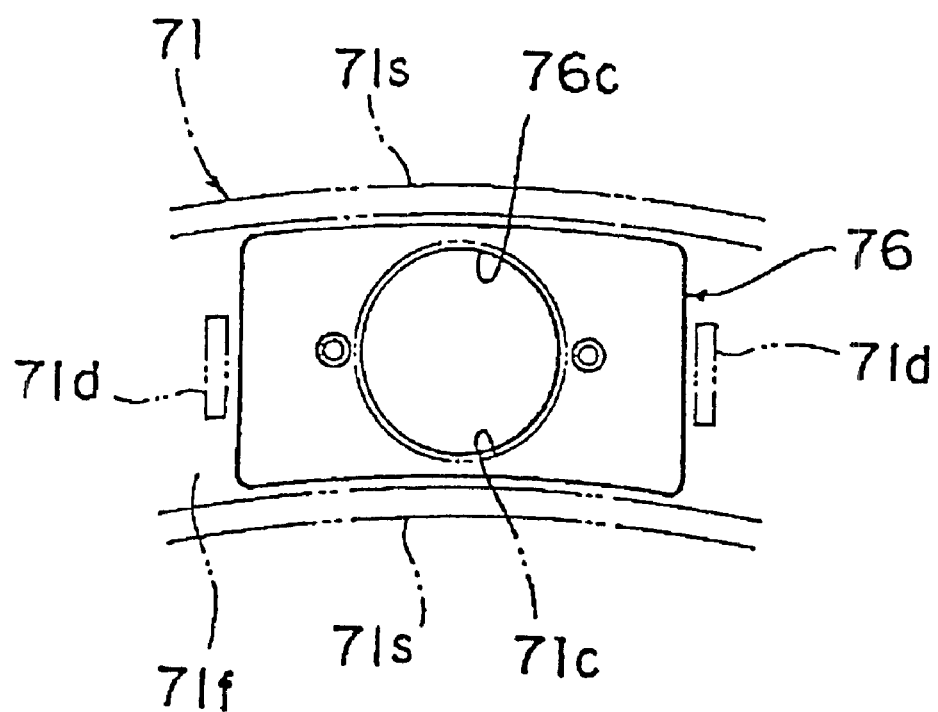
FIG. 22 is an explanatory plan view of a washer disposed on a bottom surface of the base pedestal.

A metal washer 76 is interposed between the bottom plate 71f of the base pedestal 71 and a bolt head 78H of the bolt member 78 (see FIGS. 10 and 12). FIG. 22 is an explanatory plan view of the washer 76.

Rubber or soft resin is material having excellent resiliency and sealing ability, and is used for the seal member 73 and the base packing 75. The base plate 74 and the washer 76 are made of stainless steel plate, for example. An assembling bolt in which a male screw is threaded into a portion of an outer periphery of a hollow pipe and the bolt head 78H is assembled thereto is used as the bolt member 78.

In the above structure, the unit casing 31 (i.e., base pedestal 71 and the pipe body 72) is mounted and fixed to the upper surface of the sink 21 by the following procedure.

First, the washer 76 is set through an upper opening of the base pedestal 71 on to a predetermined position of the bottom plate 71f of the base pedestal 71 (see FIG. 22). At that time, the washer 76 is precisely positioned by opposite side walls 71s and a pair of positioning projections 71d provided on the bottom plate 71f of the base pedestal 71. In this positioned state, it is preferable that the washer 76 be fastened and fixed onto the bottom plate 71f of the base pedestal 71 using a screw member having a small diameter.

Then, each of the bolt members 78 are inserted through the upper opening of the base pedestal 71, and the bolt members 78 are inserted into the washer 76 and the bolt insertion holes 76c and 71c of the bottom plate 71f of the base pedestal 71.

Next, the base plate 74 and the base packing 75 are mounted to the lower surface of the bottom plate 71f of the base pedestal 71 in this order. The screw members 77 are inserted into the screw insertion holes 74a, 75a and 71a of the base packing 75, the base plate 74 and the base pedestal 71 from the lower surface of the base pedestal 71. In this state, the seal member 73 is mounted to the upper end of the side wall 71s of the base pedestal 71, the pipe body 72 is placed thereon, and the threaded holes 72a are positioned with respect to the tip ends of the screw members 77.

Then, the screw members 77 are threadedly inserted into the corresponding threaded holes 72a of the pipe body 72 so that the pipe body 72 is assembled, fastened and fixed to the base pedestal 71 (see FIGS. 9 and 11). That is, the casing 31 of the unit body 30 is formed in this manner.

Next, the casing 31 is brought on top of the sink 21, the bolt members 78 suspending from the lower surface of the base pedestal 71 of the casing 31 are inserted into the corresponding bolt insertion holes 21h of the sink 21, and nuts 79 are threadedly engaged on the lower side of the sink 21. With this operation, the base pedestal 71 to which the pipe body 72 is integrally fixed is fastened and fixed to the upper surface of the sink 21.

As described above, the base pedestal 71 of the casing 31 of the nozzle unit 30 is made of resin, the base pedestal 71 is formed to have a substantially U-shape cross section whose upper side is opened. The pipe body 72 supported on the upper side of the base pedestal 71 is made of metal. The predetermined portions of the lower side of the pipe body 72 are provided with threaded holes 72a. The pipe body 72 is fastened and fixed to the base pedestal 71 by threadedly inserting the screw members 77 from the bottom plate 71f of the base pedestal 71. The base pedestal 71 is fastened and fixed to the sink 21 through the metal washer 76, the base plate 74 and the bolt member 78 disposed above and below the bottom plate 71f.

By employing the above fixing structure, it is possible to easily, reliably and strongly mount the nozzle unit 30 having the unit casing 31 including the resin base pedestal 71 and the metal pipe body 72 to the upper surface of the sink 21.

As shown in FIGS. 4 and 5, a metal box 15 (accommodation case) is accommodated in the upper accommodating portion 11 of the support stand 10 supporting the sink 21. The gargle bottle 41 containing gargle fluid, the soapy water bottle 42 containing soapy water and the disinfectant bottle 43 containing disinfectant are accommodated in the accommodation case 15.

The accommodating portion 11 is provided at its front surface with an open/close cover 12 which can open and close. The open/close cover 12 is provided at its back surface with a display board 13a having a manual operating function, an operation display function and the like. The accommodation case 15 is provided at its inner surface with a control board 13b (see shaded portions in FIGS. 4 and 5) having control device. The control device controls each of the pumps, the solenoid valve, chemical-out lamp and the like based on detection results of the various sensors.

Figure 7A:
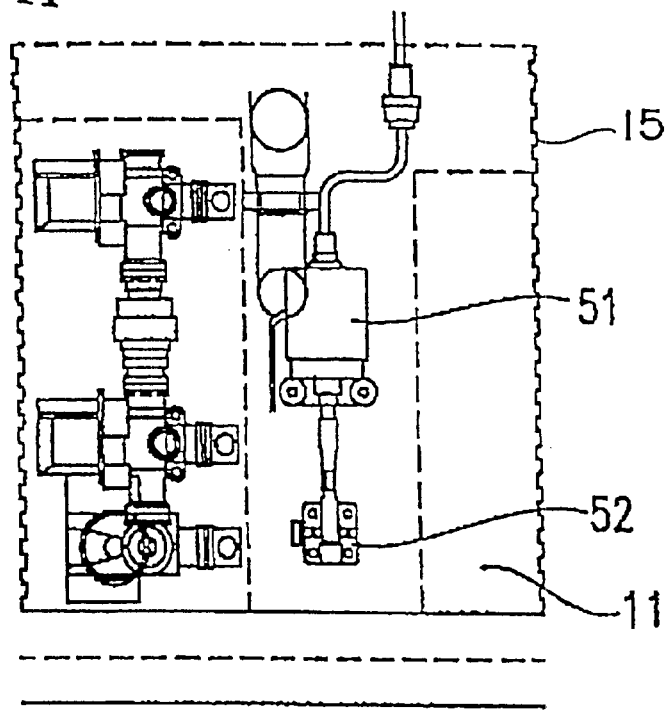
FIG. 7A is an explanatory front view showing the schematic structure of an accommodating portion of the chemical supply apparatus.
Figure 7B:
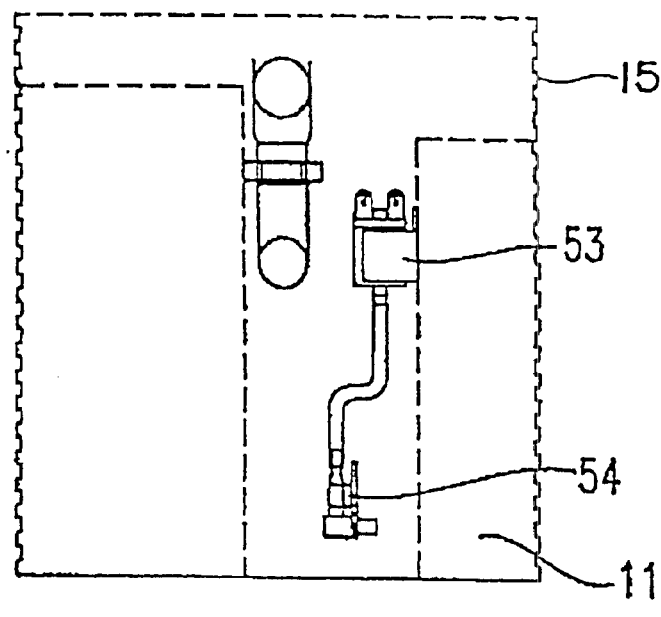
FIG. 7B is an explanatory front view showing the schematic structure of the above accommodating portion.

FIGS. 7(a) and 7(b) are schematic front views showing the accommodation case 15 in the accommodating portion 11 of the support stand 10 from which the bottles 41 to 43 are eliminated. As shown in FIG. 7(a), an electromagnetic type of disinfectant pump 51 for supplying disinfectant in the disinfectant bottle 43 to the disinfectant nozzle 38 is provided in the accommodation case 15. A disinfectant-out sensor 52 for detecting a disinfectant-out state of the disinfectant bottle 43 is also provided in the accommodation case 15. The disinfectant-out sensor 52 detects the disinfectant-out state in the disinfectant bottle 43, and if the disinfectant-out sensor 52 detects this state, the disinfectant-out lamp 31h provided on the base pedestal 71 of the nozzle unit 30 is lit.

As shown in FIG. 7(b), the electromagnetic type of gargle solenoid valve 53 for supplying gargle fluid in the gargle bottle 41 to the gargle nozzle 34, and a gargle-out sensor 54 for detecting a gargle-out state in the gargle bottle 41 are provided in the accommodation case 15. The gargle-out sensor 54 detects a gargle-out state in the gargle bottle 41. If the gargle-out sensor 54 detects this state, a gargle-out lamp 31k provided on an end surface 31c of the base pedestal 71 of the nozzle unit 30 is lit.

Figure 8:
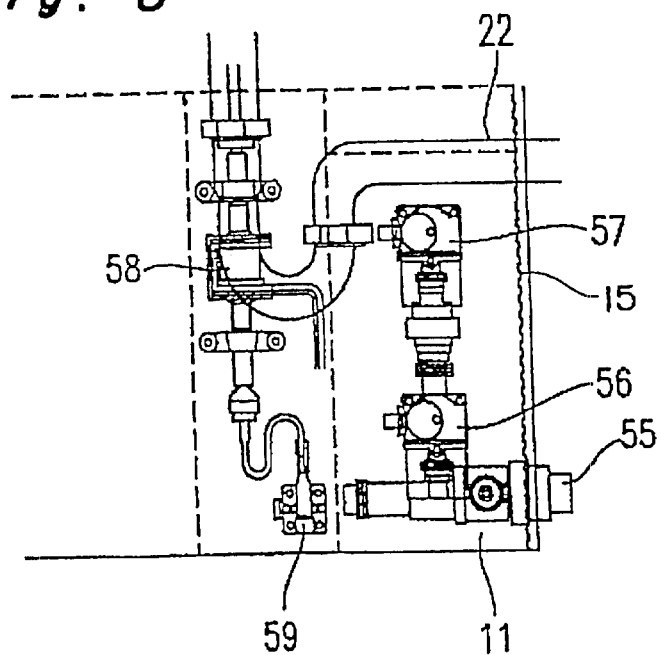
FIG. 8 is an explanatory side view showing the schematic structure of the accommodating portion.

FIG. 8 is a schematic side view showing the accommodation case 15 in the accommodating portion 11 of the support stand 10 from which the bottles 41 to 43 are eliminated. A water supply pipe 55 connected to a water supply main pipe is provided in the accommodation case 15. A water supply solenoid valve 56 which is opened when water is supplied to the water supply nozzle 32 is also provided in the accommodation case 15. A gargle supply solenoid valve 57, which is opened when water is supplied to a gargle nozzle 36, is also provided in the water supply pipe 55.

An electromagnetic type of soapy water pump 58 for supplying soapy water in the soapy water bottle 42 to the soapy water nozzle 36 is provided in the accommodation case 15. A soapy water-out sensor 59 for detecting a soapy water-out state in the soapy water bottle 42 is also provided in the accommodation case 15. The soapy water-out sensor 59 detects the soapy water-out state in the soapy water bottle 42. If the soapy water-out sensor 59 detected this state, a soapy water-out lamp 31g provided on the base pedestal 71 of the nozzle unit 30 is lit.

As described above, the base pedestal 71 of the unit casing 31 of the nozzle unit 30 is provided with the chemical-out lamps 31h, 31g and 31k as a way of indicating that the remaining amounts of chemical in each of the chemical bottles 41, 42 and 43 contain chemical. Therefore, it is possible to replenish the chemical, and to avoid a situation in which the remaining amount becomes zero and the chemical actually runs out.

The discharge nozzles 32, 34, 36, 38, the solenoid valves 53, 56, 57, the pumps 51, 58, the water supply pipe 55, the bottles 41, 42, 43, pipes between these members, and the control mechanism of the solenoid valves 53, 56, 57 and the pumps 51, 58 comprise "fluid supply mechanisms" for the fluid.

In the chemical supply apparatus A of the embodiment, basic constituent elements of each fluid supply mechanism other than discharge nozzles 32, 34, 36, 38 of each fluid supply mechanism, and pipes and electric wires disposed in the unit casing 31 of the nozzle unit 30 are accommodated in the single accommodation case 15. These basic constituent elements are connected to pipes and electric wires disposed around the accommodation case 15 as needed through connection members which are attachable and detachable with relatively simple operation.

Therefore, when maintenance work on the apparatus A is carried out, the connected state of the connection members is released, and the accommodation case 15 is pulled out from the accommodating portion 11. With this operation, the basic constituent elements in the accommodation case 15 can easily be removed.

On the other hand, when the apparatus A is assembled, the basic constituent elements of each fluid supply mechanism are assembled separately from the apparatus A, and can be accommodated in the single accommodation case 15, which enhances the working efficiency of the assembling process of each fluid supply mechanism.

The open/close cover 12 may be formed integrally together with the case 15 as an open/close cover of the accommodation case 15. In this case, the display board 13a can also be handled as one unit with the accommodation case 15.

The basic constituent elements of each assembled fluid supply mechanism can easily be moved together with the single accommodation case 15. Therefore, the assembling operation of the apparatus A is facilitated, inspection and repair work at the time of maintenance is facilitated, and service is also enhanced. Further, even if the design of the sink 21 is varied, the basic constituent elements of each fluid supply mechanism accommodated in the single accommodation case 15 can commonly be used, and efficiency when various kinds of chemical supply apparatuses A are produced can be enhanced.

According to the chemical supply apparatus having the above structure, when a user puts his or her hand near the water supply sensor 33 to discharge water from the water supply nozzle 32, the water supply solenoid valve 56 is opened, and water is discharged from the water supply nozzle 32.

Similarly, if a user puts his or her hand near the soapy water discharge sensor 37 or disinfectant discharge sensor 39 to discharge the soapy water or the disinfectant from the soapy water nozzle 36 or the disinfectant nozzle 38, the soapy water pump 58 or the disinfectant pump 51 is driven, and soapy water or disinfectant is discharged from the soapy water nozzle 36 or the disinfectant nozzle 38.

That is, the soapy water or disinfectant discharged from the soapy water nozzle 36 or the disinfectant nozzle 38 is directly discharged to the hand near the soapy water discharge sensor 37 or the disinfectant discharge sensor 39, and the user need not touch the apparatus with his or her hand.

When the user desires to gargle, the user operates the gargle fluid discharge switch 35 provided on the end surface 31c of the pipe body 72 in the casing 31 of the nozzle unit 30. With this operation, the gargle water supply solenoid valve 57 and the gargle solenoid valve 53 are opened, water is supplied to the gargle nozzle 34, vacuum is generated by the flowing water, and the gargle fluid is pumped up from the gargle bottle 41. With this, the pumped gargle fluid is mixed with water in the gargle nozzle 34, and gargle fluid diluted with water is discharged in jet.

The gargle fluid mixed and diluted with water discharged from the gargle nozzle 34 is poured in a glass and the user conducts gargling. The user may bring his or her mouth close to the gargle nozzle 34 to directly keep the gargle fluid in his or her mouth to gargle.

In gargling, excessive water discharged from the gargle nozzle 34 in jet is discharged into the recess 21a of the sink 21 from the scupper 31e formed in a lower portion of the casing 31.

In the chemical supply apparatus A of the embodiment, the nozzle unit 30 which is bent into an arc along a part of the peripheral edge of the sink recess 21a is provided on the upper surface of the periphery of the opening of the recess 21a of the sink 21. The water supply nozzle 32, the gargle nozzle 34, the soapy water nozzle 36 and the disinfectant nozzle 38 are integrally provided on the nozzle unit 30 at appropriate distances in the circumferential direction. The nozzle unit 30 is integrally provided with the water supply sensor 33, the soapy water discharge sensor 37, the disinfectant discharge sensor 39, the soapy water-out lamp 31g, the disinfectant-out lamp 31h, the gargle-out lamp 31k and the like, and the nozzle unit 30 is formed compact.

Therefore, the chemical supply apparatus A having such a structure can preferably be installed on a floor near the doorway 61 of a hall in an ordinary household. Further, the sink 21 is formed into a rectangular solid shape, and supported on the support stand 10, and the chemical supply apparatus A is excellent in design. Furthermore, the apparatus A can preferably be installed on a floor near the doorway 61 of a hall in an ordinary home.

As disclosed in Japanese Patent Application Laid-Open No. H8-299853, when the disinfectant nozzle of the apparatus is not used for the long term, dry material of the disinfectant may be removed from the inside of the nozzle. The disinfectant-out sensor 52, the gargle-out sensor 54 and the soapy water-out sensor 59 may be formed as disclosed in Japanese Patent Application Laid-open No. H8-304149.

In the infection prevention system of the present invention shown in FIG. 1 using such a chemical supply apparatus A, if a person enters into a room through the doorway 61 of the hall from outside, the human body detection sensor 62 detects the person, and outputs a predetermined signal to the voice output apparatus 63 disposed near the doorway 61. Upon reception of the signal from the human body detection sensor 62, the voice output apparatus 63 outputs a preset voice to recommend preventative action, for example, a voice "Welcome home, wash your hands and gargle" to the person who entered the room from the doorway 61. With this voice, the person who entered the room is prompted by the voice recommending gargling and washing hands, which is output from the voice output apparatus. He or she gargles and washes his or her hands using the chemical supply apparatus A before he or she takes off his or her shoes.

As described above, according to the chemical supply apparatus A, water is discharged from the water supply nozzle 32 by bringing a user's hand close to the water supply sensor 33, and the soapy water pump 58 or the disinfectant pump 51 is driven by bringing the hand close to the soapy water discharge sensor 37 or the disinfectant discharge sensor 39, and soapy water or disinfectant is discharged from the soapy water nozzle 36 or the disinfectant nozzle 38. Therefore, soapy water or disinfectant discharged from the soapy water nozzle 36 or the disinfectant nozzle 38 is directly supplied to the hand close to the soapy water discharge sensor 37 or the disinfectant discharge sensor 39.

When a user gargles, if he or she pushes the gargle switch 35 provided on the end surface 31c of the nozzle unit 30, gargle fluid is discharged from the gargle nozzle 34 in jet, and the user can gargle.

In this manner, the chemical supply apparatus A is installed on a floor close to the doorway 61, a person who enters a room is prompted to gargle and wash hands by means of a voice. Further, since it is possible to gargle and wash hands with an extremely simple operation by using the chemical supply apparatus A, a user can surely gargle and wash hands by the chemical supply apparatus A near the doorway 61 without feeling troublesome before the user takes off their shoes even immediately after the user comes home.

As a result, it is possible to prevent various bacteria, which are causes of infectious diseases, from entering an ordinary household, and it is possible to effectively prevent infection in the ordinary household. Further, it is easy to make a habit of gargling and hand washing for all the family in the ordinary household.

Further, by gargling and washing hands immediately after coming home from outside, it is possible to moderate a degree of allergy such as pollinosis.

The detection signal of a human body is normally output from the human body detection sensor 62 to the voice output apparatus 63 through wire. However, the signal may be output to the voice output apparatus 63 by a radio wave, infrared radiation or the like. The voice output apparatus 63 may not be disposed near the doorway 61, and may be provided on the chemical supply apparatus A or near the chemical supply apparatus A.

The structure of the chemical supply apparatus A provided near the doorway 61 is not limited to that shown in FIG. 1, and a fluid supply apparatus having a function of discharging disinfectant and gargle fluid may be used for a sink having a normal tap or faucet.

Further, as the chemical supply apparatus, supply mechanisms of hand washing water, warm water, soapy water, disinfectant, gargle fluid and warm air may be provided, or the chemical supply apparatus may include at least two of the mechanisms. At that time, when the chemical supply apparatus includes only a hand washing function, the disinfectant function and the gargle function may be provided separately, and the disinfection of hand fingers and gargling may be carried out utilizing a sink of the chemical supply apparatus.

Further, in the nozzle unit 30 of the above embodiment, the discharge nozzles are provided on the unit casing 31 having the integral pipe body 72 along about half of the periphery of the recess 21a of the sink 21. Alternatively, a casing having a plurality of divided pipe bodies substantially along at least a part of a peripheral shape of a sink recess may be provided, and the plurality of casings may be provided with a necessary number of discharge nozzles to form the nozzle unit. If such a divided structure is employed, it is possible to enhance flexibility of layout of nozzle unit and each nozzle.

The prevention system for preventing infectious diseases of the invention is not limited to the structure in which the chemical supply apparatus A is provided near a doorway of a hall in an ordinary household, and the chemical supply apparatus may be provided near a doorway of a building or installation in a food manufacturing factory.

The number of times in which people entering the building do not gargle or wash hands may be obtained based on the number of detection times of a human body by the human body detection sensor 62, the number of driving times of the disinfectant pump 51 provided in the accommodating portion 11 of the support stand 10, or the number of driving times of the gargle solenoid valve 53. In this case, an action for recommending gargling and hand washing is carried out for the corresponding home or installation.

As described above, the present invention is not limited to the aforementioned embodiment and is, of course, able to be subjected to various modifications, improvement in design and so on within the scope not departing from the essence thereof.

What is claimed is:

1. A fluid supply apparatus comprising:
   a sink having an upper surface and a recess in said upper surface;
   a common unit-body including a base pedestal fixed on said upper surface of said sink, at least a portion of said base pedestal being formed hollow, and said common unit-body including a pipe-shaped body mounted on said base pedestal and arranged along at least part of a far periphery of said recess opposite a near periphery of said recess closest to a user; and
   a plurality of fluid supply mechanisms for supplying different kinds of fluids, each of said fluid supply mechanisms including a respective discharge port at a predetermined location on said common unit-body disposed on an upper portion of a sink.

2. The fluid supply apparatus of claim 1, wherein said plurality of fluid supply mechanisms comprises at least two fluid supply mechanisms for supplying at least one of hand washing water, warm water, soapy water, a disinfectant, a gargle fluid, and warm air.

3. The fluid supply apparatus of claim 2, wherein each of said plurality of fluid supply mechanisms is operable to supply one of hand washing water, warm water, soapy water, a disinfectant, and a gargle fluid.

4. The fluid supply apparatus of claim 1, further comprising a detection sensor for detecting a user's operating motion to use a fluid to be supplied from a respective discharge port, said detection sensor being arranged at a vicinity of said respective discharge port and being operable to generate a signal to operate a respective one of said fluid supply mechanisms corresponding to said respective discharge port after detecting the user's operating motion so as to automatically supply fluid from said respective discharge port.

5. The fluid supply apparatus of claim 4, wherein said plurality of fluid supply mechanisms includes a gargle fluid supply mechanism for supplying a gargle fluid, said gargle fluid supply apparatus including a gargle discharge switch operable to start said gargle fluid supply mechanism so as to discharge gargle fluid from said discharge port of said gargle fluid supply mechanism.

6. The fluid supply apparatus of claim 1, wherein said plurality of fluid supply mechanisms includes a chemical fluid supply mechanism for supplying a chemical from a chemical container to a corresponding discharge port, said common unit-body further including an alarm device for providing an alarm when a remaining amount of said chemical in said chemical container is reduced below a predetermined level.

7. The fluid supply apparatus of claim 1, wherein said base pedestal of said common unit-body is formed of synthetic resin so as to have a generally U-shaped cross section with an open upper side and a lower plate, said pipe-shaped body being supported on an upper surface of said base pedestal and being formed of metal and having a threaded hole at a predetermined location in a lower part thereof, said pipe-shaped body being fastened to said base pedestal by a screw member threaded into said threaded hole from a bottom of said base pedestal, said base pedestal being fastened to said sink by metal washers and screw members arranged above and below said bottom plate of said base pedestal.

8. The fluid supply apparatus of claim 1, further comprising a single accommodation case arranged at a vicinity of said sink for accommodating elements of each fluid supply mechanism, piping elements, and electric wiring elements therein.

9. The fluid supply apparatus of claim 8, wherein all remaining basic constituent elements of each fluid supply mechanism, all remaining piping elements, and all remaining electric wiring elements not accommodated in said accommodation case are arranged inside at least one of said pipe-shaped body and said base pedestal, except that each discharge port is arranged on said pipe-shaped body.

10. The fluid supply apparatus of claim 1, wherein said sink has a substantially rectangular parallelepiped shape.

11. The fluid supply apparatus of claim 1, wherein said common unit-body is divided into a plurality of unit-body pieces arranged along said at least part of a far periphery of said recess.

12. A fluid supply apparatus comprising:

a sink having a recess;

a plurality of fluid supply mechanisms for supplying different kinds of fluids, each of said fluid supply mechanisms having a respective discharge port on an upper portion of said sink; and a plurality of detection sensors for detecting a user's operating motion to use a fluid to be supplied from a respective discharge port of a respective one of said fluid supply mechanisms, each detection sensor being arranged at a vicinity of said respective discharge port and being operable to generate a signal to operate said respective one of said fluid supply mechanisms corresponding to said respective discharge port after detecting the user's operating motion so as to automatically supply fluid from said respective discharge port;

wherein said plurality of detection sensors comprises a central detection sensor arranged at a position corresponding to an approximate center of a far periphery of said recess opposite a near periphery of said recess closest to a user, and comprises other detection sensors, said plurality of detection sensors being oriented such that a detecting direction of said central detection sensor points to an approximate center of said recess, and such that a detecting direction of each of said other detection sensors points away from said approximate center of said recess and closer to a location of the user by a predetermined angle.

13. The fluid supply apparatus of claim 12, further comprising a common unit-body, said discharge port of each fluid supply mechanism being provided at a predetermined location on said common unit-body, and said common unit-body being arranged on said upper portion of said sink.

14. The fluid supply apparatus of claim 13, wherein said common unit-body includes a base pedestal fixed onto said upper surface of said sink, and includes a pipe-shaped body mounted on said base pedestal, said discharge port of each fluid supply mechanism being provided at a predetermined location on said pipe-shaped body.

15. A prevention system for preventing infectious diseases, comprising:

a fluid supply apparatus provided with a sink and a plurality of fluid supply mechanisms for supplying different kinds of fluids, having at least a hand washing function and a gargle fluid supply function, and to be arranged near a doorway in a building;

a human body detection sensor for detecting a person entering into the building from the doorway; and a voice output apparatus for outputting a vocal sound to prompt the person to conduct gargling and hand washing when the human body detection sensor detects the person.

16. A method of preventing infectious diseases, comprising:

disposing a fluid supply apparatus near a doorway in a building, wherein the fluid supply apparatus is provided with a sink and a plurality of fluid supply mechanisms for supplying different kinds of fluids, and having at least a hand washing function and a gargle fluid supply function; and outputting a vocal sound to prompt a person to conduct gargling and hand washing when the person enters into the building from the doorway.

* * * * *